US010287397B2

(12) United States Patent
Jeletic et al.

(10) Patent No.: US 10,287,397 B2
(45) Date of Patent: May 14, 2019

(54) POLYORGANOSILOXANE COMPOSITIONS WITH METAL BASED N-HETEROCYCLIC CARBENE CONDENSATION REACTION CATALYSTS AND METHODS FOR THE PREPARATION THEREOF

(71) Applicant: Dow Corning Corporation, Midland, MI (US)

(72) Inventors: Matthew Jeletic, Freeland, MI (US); Ming-Shin Tzou, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/574,881

(22) PCT Filed: Jul. 21, 2016

(86) PCT No.: PCT/US2016/043250
§ 371 (c)(1),
(2) Date: Nov. 17, 2017

(87) PCT Pub. No.: WO2017/019426
PCT Pub. Date: Feb. 2, 2017

(65) Prior Publication Data
US 2018/0163001 A1   Jun. 14, 2018

Related U.S. Application Data

(60) Provisional application No. 62/197,124, filed on Jul. 27, 2015.

(51) Int. Cl.
| | |
|---|---|
| *C08G 77/08* | (2006.01) |
| *C08L 83/04* | (2006.01) |
| *C07F 3/06* | (2006.01) |
| *C08G 77/44* | (2006.01) |
| *C08K 3/22* | (2006.01) |
| *C08K 5/56* | (2006.01) |
| *C08G 77/16* | (2006.01) |
| *C08G 77/00* | (2006.01) |

(52) U.S. Cl.
CPC ............. *C08G 77/08* (2013.01); *C07F 3/06* (2013.01); *C08G 77/44* (2013.01); *C08K 3/22* (2013.01); *C08K 5/56* (2013.01); *C08L 83/04* (2013.01); *C08G 77/16* (2013.01); *C08G 77/80* (2013.01); *C08K 2003/2227* (2013.01)

(58) Field of Classification Search
CPC ...... C08G 77/08; B01J 31/2273; C08L 83/06; C07F 7/0836
See application file for complete search history.

(56) References Cited

U.S. PATENT DOCUMENTS

| | | | |
|---|---|---|---|
| 6,600,175 B1 | 7/2003 | Baretz et al. | |
| 6,734,465 B1 | 5/2004 | Taskar et al. | |
| 7,259,400 B1 | 8/2007 | Taskar | |
| 8,900,654 B2 | 12/2014 | Kunze et al. | |
| 8,921,493 B2 | 12/2014 | Horstman et al. | |
| 8,957,147 B2 | 2/2015 | Swier et al. | |
| 9,006,336 B2 | 4/2015 | Yang et al. | |
| 9,006,356 B2 | 4/2015 | Horstman et al. | |
| 9,006,358 B2 | 4/2015 | Horstman et al. | |
| 9,012,585 B2 | 4/2015 | Brandstadt et al. | |
| 9,150,755 B2 | 10/2015 | Maliverney et al. | |
| 2006/0255353 A1 | 11/2006 | Taskar et al. | |
| 2008/0300358 A1 | 12/2008 | Cook et al. | |
| 2009/0291238 A1 | 11/2009 | Scott et al. | |
| 2009/0299024 A1* | 12/2009 | Baceiredo | C08G 77/08 528/12 |
| 2011/0160412 A1 | 6/2011 | Thieuleux et al. | |
| 2013/0158274 A1 | 6/2013 | Maliverney et al. | |
| 2013/0245187 A1 | 9/2013 | Swier et al. | |
| 2014/0008697 A1 | 1/2014 | Harkness et al. | |
| 2014/0100347 A1 | 4/2014 | Cook et al. | |
| 2014/0227449 A1 | 8/2014 | Maliverney et al. | |
| 2015/0210809 A1 | 7/2015 | Brandstadt et al. | |
| 2016/0137774 A1 | 5/2016 | Schmidt et al. | |

FOREIGN PATENT DOCUMENTS

| | | |
|---|---|---|
| CN | 103145753 | 6/2013 |
| KR | 20090048542 | 5/2009 |
| WO | 2006060141 | 6/2006 |
| WO | 2013184076 | 12/2013 |

OTHER PUBLICATIONS

Budagumpi, et. al. "Group XII Metal-N-Heterocyclic Carbene Complexes: Synthesis, Structural Diversity, Intramolecular Interactions, and Applications" Organometallics, 2013, vol. 32, pp. 1537-1562, American Chemical Society.

Dyson, et al. "Synthesis of Rhodiu(I) and iridium (I) complexes of chiral N-heterocyclic cargenes and their application to asymmetric transfer hydrogenation" The Royal Society of Chemistry, Dalton Trans., 2009, 7141-7151.

Zhang, et. al. "N-heterocyclic carbene (NHC) complexes of group 4 transition metals" The Royal Society of Chemistry 2015, Chem Soc. Rev., 2015, 44, 1898-1921. [See GIPS LAN folder for copy].

* cited by examiner

*Primary Examiner* — Kuo Liang Peng
(74) *Attorney, Agent, or Firm* — Catherine U. Brown

(57) ABSTRACT

A complex prepared by combining a metal compound and an N-heterocyclic carbene has catalytic activity for condensation reaction of polyorganosiloxane compositions. The composition includes the complex, a silanol functional compound having an average per molecule of one or more silicon bonded hydroxy moieties.

19 Claims, No Drawings

US 10,287,397 B2

POLYORGANOSILOXANE COMPOSITIONS WITH METAL BASED N-HETEROCYCLIC CARBENE CONDENSATION REACTION CATALYSTS AND METHODS FOR THE PREPARATION THEREOF

CROSS REFERENCE TO RELATED APPLICATIONS

This application is a U.S. national stage filing under 35 U.S.C. § 371 of PCT Application No. PCT/US16/043250 filed on 21 Jul. 2016, which claims the benefit of U.S. Provisional Patent Application No. 62/197,124 filed 27 Jul. 2015 under 35 U.S.C. § 119 (e). PCT Application No. PCT/US16/043250 and U.S. Provisional Patent Application No. 62/197,124 are hereby incorporated by reference.

BACKGROUND

Bases used as condensation reaction catalysts such as 1,8-Diazabicyclo[5.4.0]undec-7-ene (DBU); 1,5-Diazabicyclo[4.3.0]non-5-ene; 1,4-Diazabicyclo[2.2.2]octane (DABCO); and others suffer from the drawback of inhibition of catalysis when a filler is added to a composition containing such catalyst. Metallic condensation reaction catalysts (such as acetyl acetonates of aluminum or zinc) suffer from the drawback of causing scission of aromatic groups from siloxane resins, particularly resin-linear compounds. There is an industry need for catalysts that can deliver controlled cure of siloxane compounds, including resin-linear compounds, via condensation reaction in the presence of untreated fillers, such as phosphors.

BRIEF SUMMARY OF THE INVENTION

A metal compound and an N-heterocyclic carbene ligand are used to prepare a condensation reaction catalyst. A composition comprises the catalyst and a silanol-functional compound having an average, per molecule, of one or more silicon bonded hydroxy moieties capable of undergoing condensation reaction.

DETAILED DESCRIPTION OF THE INVENTION

All amounts, ratios, and percentages are by weight unless otherwise indicated. The Brief Summary of the Invention and the Abstract are hereby incorporated by reference. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an alkenyl group, or an aryl group includes the member alkyl individually; the subgroup alkyl and aryl; and any other individual member and subgroup subsumed therein.

Abbreviations used herein are defined as follows. The abbreviation "cP" means centiPoise. "DP" means the degree of polymerization of a polymer. "FTIR" means Fourier transform infrared spectroscopy. "GPC" means gel permeation chromatography. "Mn" means number average molecular weight. Mn may be measured using GPC. "Mw" means weight average molecular weight. "NHC" means N-heterocyclic carbene. "NMR" means nuclear magnetic resonance. "Me" means methyl. "Et" means ethyl. "Ph" means phenyl. "Pr" means propyl and includes various structures such as iPr and nPr. "iPr" means isopropyl. "nPr" means normal propyl. "Bu" means butyl and includes various structures including nBu, sec-butyl, tBu, and iBu. "iBu" means isobutyl. "nBu" means normal butyl. "tBu" means tert-butyl.

Component i), a metal compound, and component ii), an N-heterocyclic carbene (NHC), are used to prepare ingredient (A) a condensation reaction catalyst. A composition comprises ingredient (A) the catalyst and ingredient (B) a silanol functional compound having an average, per molecule, of one or more silicon bonded hydroxy moieties.

Component i) Metal Compound

The metal compound comprises a metal atom selected from titanium (Ti) and zinc (Zn) and one or more substituents coordinated with the metal atom, with the proviso that the one or more substituents coordinated with the metal atom of component i) are distinct from the N-heterocyclic carbene (NHC), i.e., different from the NHC as defined for component ii). As used herein, "coordinated with" refers to any means of chemically bonding the metal atom and the substituent, including dative bonding, covalent bonding, or ionic bonding. Alternatively, the metal atom in the metal compound may be Zn. The metal compound may have general formula (P): M-$R_a$, where M is the metal (Ti or Zn), each R is a substituent coordinated with the metal atom, and subscript a represents 1 to the maximum number of coordination sites for the metal selected for M. Each R may be independently selected from a halogen atom, a monovalent hydrocarbon group, an amino group, a silyl amide group, a carboxylate ester group, or a hydrocarbonoxy group. Alternatively, two or more instances of R may be bound together to occupy two or more coordination sites on the metal selected for M. The halogen atom for R may be F, Cl, Br, or I; alternatively F or Cl; alternatively Cl or Br; and alternatively Cl.

Examples of monovalent hydrocarbon groups for R include, but are not limited to, an alkyl group such as Me, Et, Pr, Bu, pentyl, hexyl, heptyl, ethylhexyl, octyl, decyl, dodecyl, undecyl, and octadecyl; an alkenyl group such as vinyl, allyl, propenyl, and hexenyl; an alkynyl group such as propynyl; and an aryl group such as phenyl, tolyl, xylyl, mesityl, naphthyl, anthryl, or benzyl; and an aralkyl group such as 1-phenylethyl or 2-phenylethyl. Alkyl groups may be branched or unbranched. For example, propyl may be n-propyl or iso-propyl and butyl may be n-butyl, iso-butyl, tert-butyl, or sec-butyl. Alternatively, the alkyl group may be methyl, ethyl, propyl, or butyl.

Examples of amino groups for R have formula —$NR'_2$, where each R' is independently a hydrogen atom or a monovalent hydrocarbon group. Exemplary monovalent hydrocarbon groups for R' include, but are not limited to, alkyl, alkenyl, aryl, or aralkyl groups as described above for R. Alternatively, each R' may be a hydrogen atom or an alkyl group of 1 to 4 carbon atoms, such as methyl or ethyl.

Alternatively, for R in general formula (P) the silylamide group may have general formula —$N(SiR'''_3)_2$, where each R''' is independently a monovalent hydrocarbon group.

Examples of monovalent hydrocarbon groups for R''' include, but are not limited to, alkyl, alkenyl, aryl, or aralkyl groups as described above for R. Alternatively, each R''' may be an alkyl group, and alternatively each R''' may be methyl, ethyl, propyl, or butyl.

Alternatively, each R in general formula (P) may be a carboxylate ester group. Examples of suitable carboxylate ester groups for R include, but are not limited to ethyl-hexanoate (such as 2-ethylhexanoate), neodecanoate, octanoate, and stearate.

Examples of monovalent hydrocarbonoxy groups for A may have formula —O—R'', where R'' is a monovalent hydrocarbon group. Examples of monovalent hydrocarbon groups for R'' include, but are not limited to, alkyl, alkenyl, and aryl as described above for R. Alternatively, each R'' may be an alkyl group, such as methyl, ethyl, propyl, or butyl such as n-butyl, iso-butyl, or t-butyl. Alternatively, each R'' may be an alkyl group, and alternatively each R'' may be ethyl, propyl, or butyl.

Alternatively, the metal compound may be a complex that does not include a NHC ligand. For example, the metal compound may be a metal betadiketonate, such as a zinc betadiketonate exemplified by Zn(II) acetyl acetonate or a titanium betadiketonate.

Alternatively, in formula (P) above each R may be an alkyl group. Alternatively in general formula (P), each R may be selected from the group consisting of Cl, ethyl, benzyl, mesityl, phenyl, —$NEt_2$, cyclooctadiene, ethoxide, iso-propoxide, butoxide, 2-ethylhexanoate, neodecanoate, octanoate, and stearate. Alternatively, each R may be independently selected from a silyl amide group, a halogen atom, an alkyl group, and an alkoxy group. Alternatively, each R may be a halogen atom.

Titanium compounds suitable for use as component i) are commercially available. For example, Titanium(IV) ethoxide and Titanium(IV) isopropoxide are available from Strem Chemicals Inc. of Newburyport, Mass., U.S.A. Titanium (IV) n-butoxide and Titanium(IV) t-butoxide are available from Sigma-Aldrich of St. Louis, Mo., U.S.A. Amino compounds of titanium, such as $Ti(NMe_2)_4$ and $Ti(NEt_2)_4$, are also commercially available from Strem Chemicals, Inc. Ingredient (A) may comprise an aralkyl compound of titanium, such as tetrabenzyl titanium, which is commercially available from MCAT GmbH of Universitätsstrasse 10, 78457 Konstanz, Gebäude L, Germany.

Zinc compounds suitable for use as component i) are commercially available. For example, dialkyl zinc compounds such as $Zn-Et_2$ and diaryl zinc compounds such as $Zn-Ph_2$ are commercially available from Sigma-Aldrich of St. Louis, Mo., U.S.A. (Aldrich). Zinc(II) bis(trialkylsilyl) amides such as zinc bis(bis(trimethylsilyl)amide) is also commercially available from Aldrich. Diesters of zinc, such as $Zn(octanoate)_2$, are commercially available from City Chemicals LLC of West Haven, Conn., U.S.A. Zinc 2-ethylhexanoate is commercially available from Strem Chemicals, Inc. of Newburyport, Mass., U.S.A. Halides of zinc, such as $ZnCl_2$ are available from Aldrich. Zinc(II) acetyl acetonate is also commercially available.

Alternatively, the metal compound selected for component i) may be a halide, e.g., $ZnCl_2$; a dialkyl zinc, e.g., diethyl zinc, or a complex of the metal with one or more ligands other than the NHC ligand, e.g., Zn (II) acetyl acetonate. Component i), the metal compound, does not include an N-heterocyclic carbene.

Component ii) N-Heterocyclic Carbene

Component ii) is an N-heterocyclic carbene (NHC). Without wishing to be bound by theory, it is thought that the carbene functionality of component ii) coordinates with the metal atom and/or the NHC displaces one or more instances of substituent R in component i), the metal compound described above, to form a metal-N-heterocyclic carbene complex (M-NHC complex).

The N-heterocyclic carbene has general formula (I):

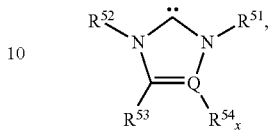

where Q is a nitrogen atom (N) or a carbon atom (C); subscript x is 0 when Q is N, and subscript x is 1 when Q is C; one of $R^{51}$ and $R^{52}$ is an alkyl group and the other of $R^{51}$ and $R^{52}$ is selected from the group consisting of an alkyl group, an hydroxy functional group, a carboxylic acid functional group, and a substituted or unsubstituted hydroxy functional aromatic group; and $R^{53}$ and $R^{54}$ are each independently selected from a hydrogen atom, an alkyl group, an alkenyl group, an alkynyl group, or an aryl group as described above for R, with the proviso that $R^{53}$ and $R^{54}$ may optionally bond together to form a fused ring structure. Suitable hydrocarbyl groups for $R^{51}$ include an alkyl group (such as methyl, ethyl, propyl or butyl), aryl (such as phenyl, tolyl, or mesityl), or aralkyl, (such as 1-phenylethyl, 2-phenylethyl, or 2,6-diisopropylphenyl). Alternatively, $R^{51}$ may be an alkyl group, such as an alkyl group of 1 to 6 carbon atoms, alternatively 1 to 4 carbon atoms. The alkyl group for $R^{52}$ may be an alkyl group of 1 to 6 carbon atoms, and alternatively 1 to 4 carbon atoms. Alternatively, the alkyl group for $R^{52}$ and/or $R^{51}$ may be selected from methyl, ethyl, propyl, or butyl. The hydroxy functional group for $R^{52}$ may have formula —$(CH_2)_yOH$, where subscript y is 1 to 3, alternatively y 1 to 2, and alternatively y=1. The carboxylic acid functional group for $R^{52}$ may have formula —$(CH_2)_zC(O)OH$ where subscript z is 1 to 3, alternatively z is 1 to 2, and alternatively z=1. The substituted or unsubstituted hydroxy functional aromaticgroup for $R^{52}$ has formula:

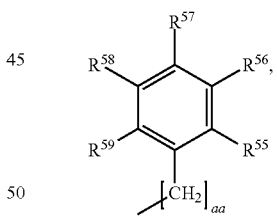

where each of $R^{55}$, $R^{56}$, $R^{57}$, $R^{58}$, and $R^{59}$ are independently selected from a hydrogen atom, an alkyl group of 1 to 6 carbon atoms, or a hydroxyl group, with the proviso that at least one of $R^{55}$, $R^{56}$, $R^{57}$, $R^{58}$, and $R^{59}$ is a hydroxyl group. Subscript aa is 1 to 3; alternatively aa is 1 to 2; and alternatively aa=1. Alternatively, $R^{55}$ is a hydroxyl group, $R^{56}$ and $R^{58}$ are each alkyl groups such as butyl, and $R^{57}$ and $R^{59}$ are each hydrogen atoms. When one of $R^{55}$, $R^{56}$, $R^{57}$, $R^{58}$, and $R^{59}$ is a hydroxyl group and the others are each hydrogen, the hydroxy functional aromatic group is unsubstituted. When one of $R^{55}$, $R^{56}$, $R^{57}$, $R^{58}$, and $R^{59}$ is a hydroxyl group and one or more of $R^{55}$, $R^{56}$, $R^{57}$, $R^{58}$, and $R^{59}$ which is not the hydroxyl group is a substituent other than hydrogen, then the hydroxy functional aromatic group is substituted.

In one embodiment, the NHC is an imidazole based N-heterocyclic carbene, i.e., when in formula (I) above Q is a carbon atom, and subscript x is 1. The imidazole based N-heterocyclic carbene ligand has formula (II):

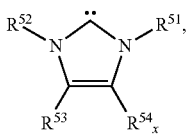

where $R^{51}$, $R^{52}$, $R^{53}$ and $R^{54}$ are as described above.

Alternatively, the imidazole based N-heterocyclic carbene ligand may have general formula (III):

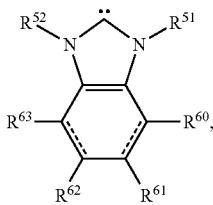

where $R^{51}$ and $R^{52}$ are as described above, and $R^{60}$, $R^{61}$, $R^{62}$, and $R^{63}$ are each independently selected from a hydrogen atom, an alkyl group, an alkenyl group, and an alkynyl group (as described above for R) and each dashed line represents that a single bond or a double bond may be present in the ring. Alternatively, each dashed line indicates a double bond, and $R^{60}$, $R^{61}$, $R^{62}$, and $R^{63}$ are hydrogen or an alkyl selected from methyl, ethyl, propyl or butyl, as described above for R.

Alternatively, the NHC may be a triazole, i.e., when in formula (I) above, Q is N and subscript x is 0. The triazole may have formula (IV):

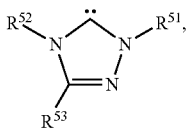

where $R^{51}$, $R^{52}$, and $R^{53}$ are as described above.

Examples of compounds for component ii) include but are not limited to 1,3-di-1-adamantylimidazol-2-ylidene; 1,3,4,5-tetramethylimidazol-2-ylidene; and 1,3-bis(2,6-diisopropylphenyl)imidazol-2-ylidene. These NHCs are commercially available.

Alternatively, component ii) may be prepared rather than purchased, e.g., by combining an azolium salt with a base, before adding component i). Suitable azolium salts for preparing the NHCs described above include benzimidizolium salts, imidizolium salts, and triazolium salts. The anion in the azolium salt may be a halide such as chloride, bromide, or iodide; or a borate such as tetrafluoroborate. Suitable azolium salts are exemplified by 1,3-dimesitylimidazolium halide; 1,3-bis(2,6-diisopropylphenyl)-imidazolium halide; 3-butyl-1-methylimidazolium halide; and 3-butyl-1-methylimidazolium tetrafluoroborate. Suitable bases may be organic soluble bases and inorganic bases, including but not limited to, cesium salts such as cesium carbonate or cesium acetate, KH, K(N(SiMe$_3$)$_3$)$_2$, NaOH, KOH, pyridine, lithiumdiisopropylamide, potassium t-butoxide, NaH, or LiN(SiMe$_3$)$_2$. The azolium salt and the base may be combined by any convenient means, such as mixing them together at or below room temperature (RT) of 25° C. (e.g., −70° C. to 25° C.) for at least 30 minutes, alternatively 30 minutes to 14 hours.

Ingredient (A) may be prepared by a method comprising combining components i) and ii) described above. Without wishing to be bound by theory, it is thought that this will form a metal-N-heterocyclic carbene complex (M-NHC complex). The method may optionally further comprise a step of dissolving either component i), component ii), or both components i) and ii), in a solvent before combining them. Suitable solvents are exemplified by those described below for ingredient (S). Alternatively, the component ii) may be dissolved in a solvent in a container, and the solvent may thereafter be removed before adding component i) to the container with the component ii). The amounts of component i) and component ii) are selected such that the mole ratio of component ii) to component i) (Ligand:Metal Ratio) may range from 1:1 to 10:1, alternatively 1:1 to 3:1, and alternatively 1:1 to 2:1. Combining components i) and ii) may be performed by any convenient means, such as mixing them together in or shaking the container.

Combining component i) and component ii) may be performed by any convenient means such as allowing component i) and component ii) prepared as described above to react at or below room temperature (RT) of 25° C. for a period of time, or by heating for a period of time. Heating may be performed by any convenient means, such as via a heating mantle, heating coil, or placing the container in an oven. The reaction temperature depends on various factors including the reactivities of the specific component i) and component ii) selected and the Ligand:Metal Ratio, however, temperature may range from −70° C. to 100° C., alternatively −70° C. to 25° C. Reaction time depends on various factors including the reaction temperature selected, however, reaction time may range from 1 minute to 48 hours, alternatively 45 minutes (min) to 60 min. Component i) and component ii) may be combined and heated sequentially. Alternatively, component i) and component ii) may be combined and heated concurrently.

The method of preparing ingredient (A) may optionally further comprise adding a solvent after the reaction. Suitable solvents are exemplified by those described below for ingredient (S). Alternatively, the method may optionally further comprise removing a reaction by-product and/or the solvent, if the solvent is present (e.g., used to facilitate combination of component i) and the component ii)). Whether a by-product forms, and if so its identity, will depend on various factors including the selection of components i) and ii) and the synthesis method of component ii) and the complex of ingredient (A). However, by-products may include, for example, H—R (where R is as defined above in general formula (P)) or an inorganic side product and/or a protonated base, species formed from the cation of the base and anion of the azoluim salt or a species formed form an anion of the azoluim salt and R, when an azolium salt is used, or any species resulting from reacting a substituent off component i) when component ii) reacts with component i). By-products may be removed by any convenient means, such as precipitation and filtering, recrystallization, or sublimation, with heating or under vacuum, or a combination thereof. The resulting isolated M-NHC complex may be used as the catalytically active reaction product of ingredient (A).

Alternatively, the reaction by-products are not removed before using the catalytically active reaction product as ingredient (A). For example, component i) and component ii) may be reacted as described above, with or without solvent removal, and the resulting catalytically active reaction product (comprising the metal-ligand complex and the reaction by-product and optionally a solvent or diluent) may be used as ingredient (A). Without wishing to be bound by theory, it is thought that a by-product may act as a condensation reaction catalyst in addition to the M-NHC complex, or as a co-catalyst or an activator for the M-NHC complex. Therefore, the reaction product may catalyze a condensation reaction.

(A) Complex

The condensation reaction catalyst, ingredient (A), comprises a M-NHC complex. The M-NHC complex may have the general formula (V): $[ML_n][A]_y$, where M is Zn or Ti as described above, each ligand, L, is any substituent described above for R in general formula (P), with the proviso that at least one L is an NHC ligand and subscript n is 1 to the maximum coordination sites, depending on the denticity of the substituent for L. Examples where n=6 include any of the following combinations; 6 monodentate ligands, 4 monodentate ligands+1 bidentate ligand, 3 monodentate ligands+1 tridentate ligand, 2 monodentate ligands+2 bidentate ligands, 2 monodentate ligands+1 tetradentate ligand, 1 monodentate ligand+1 pentadentate ligand, 1 monodentate ligand+1 bidentate ligand+1 tridentate ligand, 3 bidentate ligands, 2 tridentate ligands, 1 hexadentate ligand, or 1 bidentate ligand+1 tetradentate ligand. Examples where n=5 include any of the following combinations; 5 monodentate ligands, 3 monodentate ligands+1 bidentate ligand, 2 monodentate ligand+1 tridentate ligand, 1 monodentate ligand+2 bidentate ligand, 1 monodentate ligand+1 tetradentate ligand, 1 bidentate ligand+1 tridentate ligand, or 1 pentadentate ligand. Examples where n=4 include any of the following combinations; 4 monodentate ligands, 2 monodentate ligands+1 bidentate ligand, 2 bidentate ligands, 1 monodentate ligand+1 tridentate ligand, or 1 tetradentate ligand. Examples where n=3 include any of the following combinations; 3 monodentate ligands, 1 monodentate ligand+1 bidentate ligand, or 1 tridentate ligand. Examples where n=2 include any of the following combinations; 2 monodentate ligands or 1 bidentate ligand. Examples where n=1 include 1 monodentate ligand. The NHC ligand can be monodentate to tridentate. For example, the NHC ligand of general formula (I) may be monodentate, where $R^{51}$ and $R^{52}$ are each methyl, Q, $R^{53}$, and $R^{54}$ are as described above. Alternatively, the NHC ligand of general formula (I) may be bidentate, for example when one of $R^{51}$ and $R^{52}$ has more than one carbon atom. And, the NHC ligand of general formula (III) may be tridentate, for example, when both of $R^{51}$ and $R^{52}$ have more than one carbon atom. $[A]_y$ represents an unbound anion species to make the overall charge of the complex zero, where subscript y may be 0 to 2 for Zn and 0 to 4 for Ti. In general formula (V), A represents an unbound anion species. Examples of A include, but are not limited to, cyanide, iodide, bromide, chloride, fluoride, nitrate, nitrite, phosphate, phosphite, sulfate, sulfite, triflate, tosylate, brosylate, nosylate, sulfonate, formate, oxalate, acetate, thiosulfate, hydroxide, carbonate, bicarbonate, bisulfate, bisulfite, chlorate, chlorite, perchlorate, hypochlorite or any combination thereof. The M-NHC complex is distinct from (different from) component (i) and component (ii), described above.

Ingredient (A), described above, is capable of catalyzing condensation reaction of hydroxy groups. Therefore, ingredient (A) may be used in a composition comprising ingredient (A), as described above, and ingredient (B) a silanol functional compound having one or more silicon bonded hydroxy (Si—OH) moieties per molecule. The composition may optionally further comprise one or more additional ingredients. The one or more additional ingredients are distinct from (different from) ingredients (A) and (B). Suitable additional ingredients are exemplified by (C) a cross-linker, (D) a drying agent; (E) an extender, a plasticizer, or a combination thereof; (F) a filler; (G) a filler treating agent; (H) a biocide; (J) a flame retardant; (K) a surface modifier; (L) a chain lengthener; (M) an endblocker; (N) a nonreactive binder; (O) an anti-aging additive; (P) a water release agent; (Q) a pigment; (R) a rheological additive; (S) a vehicle (such as a solvent and/or a diluent); (T) a tackifying agent; (U) a corrosion inhibitor; and a combination thereof. Ingredients (C), (D), (E), (F), (G), (H), (J), (K), (L), (M), (N), (O), (P), (Q), (R), (S), (T), and (U) are described and exemplified, for example, in U.S. Patent Publication 2014/0371056, which is hereby incorporated by reference for the purpose of describing examples of ingredients (C), (D), (E), (F), (G), (H), (J), (K), (L), (M), (N), (O), (P), (Q), (R), (S), (T), and (U). Alternatively, the composition may comprise ingredients (A), (B), and (F). Alternatively, the composition may comprise ingredients (A), (B), (C), and (F). Alternatively, the composition may comprise ingredients (A), (B), (F), and (G). Alternatively, the composition may comprise ingredients (A), (B), (C), (F), and (G).

Ingredient (A) is present in the composition in a catalytically effective amount. The exact amount depends on various factors including reactivity of ingredient (A), the type and amount of ingredient (B), and the type and amount of any additional ingredient, if present. However, the amount of ingredient (A) in the composition may range from 1 part per million (ppm) to 5%, alternatively 0.1% to 2%, and alternatively 1 ppm to 1%, based on total weight of all ingredients in the composition.

The composition may contain one single catalyst. Alternatively, the composition may comprise two or more catalysts described above as ingredient (A), where the two or more catalysts differ in at least one property such as selection of NHC ligand for component ii), selection of metal compound for component i), Ligand:Metal Ratio, and definitions for substituent R.

Ingredient (B)

Ingredient (B) is a silanol functional compound having an average, per molecule, of one or more silicon bonded hydroxy (Si—OH) moieties, alternatively two or more Si—OH moieties. Ingredient (B) may contain additional functional groups (i.e., one or more functional groups other than Si—OH), such as carboxyl, amino, urea, carbamate, amide, or epoxy. Ingredient (B) may have two Si—OH moieties per molecule. Alternatively, ingredient (B) may have an average of more than one Si—OH moieties per molecule, alternatively 2 or more Si—OH moieties per molecule, and alternatively 10 to 1000 Si—OH moieties per molecule. Ingredient (B) may be selected from a polyorganosiloxane such as a polydiorganosiloxane or a silicone-organic copolymer having the one or more Si—OH moieties with the OH covalently bonded to a Si atom in the polymer backbone and/or terminus. Alternatively ingredient (B) may be a polyorganosiloxane. The Si—OH moiety in ingredient (B) may be located at terminal, pendant, or both terminal and pendant positions in the compound. Ingredient (B) may comprise a linear, branched, cyclic, or resinous structure. Alternatively, ingredient (B) may comprise a linear, branched or cyclic structure. Alternatively, ingredient (B) may comprise a linear or branched structure. Alternatively, ingredient (B) may comprise a linear structure. Alternatively, ingredient (B) may comprise a linear structure and a resinous structure. Ingredient (B) may comprise a homopolymer or a copolymer or a combination thereof.

Ingredient (B) may have the Si—OH moieties contained in groups of the formula (i):

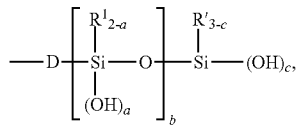

where each D independently represents an oxygen atom, a divalent organic group, a divalent silicone organic group, or a combination of a divalent hydrocarbon group and a divalent siloxane group; each $R^1$ independently represents a monovalent hydrocarbon group; subscript c represents 0, 1, 2, or 3; subscript a represents 0, 1, or 2; and subscript b has a value of 0 or greater, with the proviso that the sum of (a+c) is at least 1, such that, on average, at least one hydroxy group is present in the formula. Alternatively, subscript b may have a value ranging from 0 to 18.

Alternatively, each D may be independently selected from an oxygen atom and a divalent hydrocarbon group. Alternatively, each D may be an oxygen atom. Alternatively, each D may be a divalent hydrocarbon group exemplified by an alkylene group such as ethylene, propylene, butylene, or hexylene; an arylene group such as phenylene, or an alkylarylene group such as:

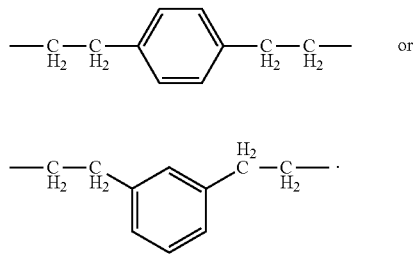

Alternatively, an instance of D may be an oxygen atom while a different instance of D is a divalent hydrocarbon group.

Alternatively, each $R^1$ in the formula above may be independently selected from alkyl groups of 1 to 20 carbon atoms, aryl groups of 6 to 20 carbon atoms, and aralkyl groups of 7 to 20 carbon atoms.

Alternatively, subscript b may be 0.

Ingredient (B) may comprise the groups described by formula (i) above in an amount of the base polymer ranging from 0.2 mole % to 10 mole %, alternatively 0.5 mole % to 5 mole %, alternatively 0.5 mole % to 2.0 mole %, alternatively 0.5 mole % to 1.5 mole %, and alternatively 0.6 mole % to 1.2 mole %.

Ingredient (B) may be a polyorganosiloxane with a linear structure, i.e., a polydiorganosiloxane. When ingredient (B) is a polydiorganosiloxane, ingredient (B) may comprise a hydroxy-endblocked polydiorganosiloxane, a hydroxysilyl-hydrocarbylene-endblocked polydiorganosiloxane, or a combination thereof.

Ingredient (B) may comprise a polydiorganosiloxane of formula (I):

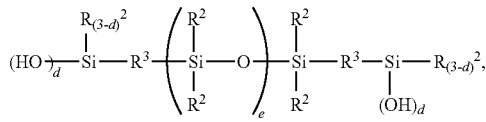

where each $R^2$ is independently a monovalent organic group, each $R^3$ is independently an oxygen atom or a divalent hydrocarbon group, each subscript d is independently 1, 2, or 3, and subscript e is an integer having a value sufficient to provide the polydiorganosiloxane with a viscosity of at least 100 mPa·s at 25° C. and/or a DP of at least 87. DP may be measured by GPC using polystyrene standards calibration. Alternatively, subscript e may have a value ranging from 1 to 200,000.

Suitable organic groups for $R^2$ include, but are not limited to, monovalent organic groups such as hydrocarbon groups and halogenated hydrocarbon groups. Examples of monovalent hydrocarbon groups for $R^2$ include, but are not limited to, alkyl such as methyl, ethyl, propyl, pentyl, octyl, decyl, dodecyl, undecyl, and octadecyl; cycloalkyl such as cyclopentyl and cyclohexyl; aryl such as phenyl, tolyl, xylyl, and benzyl; and aralkyl such as 1-phenylethyl or 2-phenylethyl. Examples of monovalent halogenated hydrocarbon groups for $R^2$ include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups for $R^2$ include, but are not limited to, hydrocarbon groups substituted with oxygen atoms such as glycidoxyalkyl, and hydrocarbon groups substituted with nitrogen atoms such as aminoalkyl and cyano-functional groups such as cyanoethyl and cyanopropyl. Alternatively, each $R^2$ may be an alkyl group such as methyl.

Ingredient (B) may comprise an α,ω-difunctional-polydiorganosiloxane when, in formula (I) above, each subscript d is 1 and each $R^3$ is an oxygen atom. For example, ingredient (B) may have formula (II): $HOR^2_2SiO$—$(R^2_2SiO)_{e'}$—$SiR^2_2OH$, where $R^2$ is as described above and subscript e' is an integer having a value sufficient to give the polydiorganosiloxane of formula (II) the viscosity described above. Alternatively, subscript e' may have a value ranging from 1 to 200,000, alternatively 50 to 1,000, and alternatively 200 to 700.

Alternatively, in formula (II) described above, each $R^2$ may be an alkyl group such as methyl, and subscript e' may have a value such that the hydroxy functional polydiorganosiloxane has a viscosity of at least 100 mPa·s at 25° C. Alternatively, subscript e' may have a value ranging from 50 to 700. Exemplary hydroxy-endblocked polydiorganosiloxanes are hydroxy-endblocked polydimethylsiloxanes. Hydroxy-endblocked polydiorganosiloxanes suitable for use as ingredient (B) may be prepared by methods known in the art, such as hydrolysis and condensation of the corresponding organohalosilanes or equilibration of cyclic polydiorganosiloxanes.

Alternatively, ingredient (B) may have a silicone-organic block copolymer backbone, which comprises at least one block of polyorganosiloxane groups and at least one block of an organic polymer chain and at least one group of formula (i) described above, alternatively two or more groups of formula (i). The polyorganosiloxane groups may comprise groups of formula —$(R^4_f SiO_{(4-f)/2})$—, in which each $R^4$ is independently a group of formula (i), an organic group such as a hydrocarbon group having from 1 to 18 carbon atoms, a halogenated hydrocarbon group having from 1 to 18 carbon atoms such as chloromethyl, perfluorobutyl, trifluoroethyl, and nonafluorohexyl, a hydrocarbonoxy group having up to 18 carbon atoms, or another organic group exemplified by an oxygen atom containing group such as (meth)acrylic or carboxyl; a nitrogen atom containing group such as amino-functional groups, amido-functional groups, and cyano-functional groups; a sulfur atom containing group such as mercapto groups; and subscript f has, on average, a value ranging from 1 to 3, alternatively 1.8 to 2.2. Alternatively, the silicone-organic block copolymer may be terminated with groups of formula (i).

Alternatively, each $R^4$ may be a hydrocarbon group having 1 to 10 carbon atoms or a halogenated hydrocarbon group; and subscript f may be 0, 1 or 2. Examples of groups suitable for $R^4$ include Me, Et, Pr, Bu, vinyl, cyclohexyl, phenyl, tolyl group, a propyl group substituted with chlorine or fluorine such as 3,3,3-trifluoropropyl, chlorophenyl, beta-(perfluorobutyl)ethyl or chlorocyclohexyl group.

The organic blocks in the polymer backbone may comprise, for example, polystyrene and/or substituted polystyrenes such as poly(α-methylstyrene), poly(vinylmethylstyrene), dienes, poly(p-trimethylsilylstyrene) and poly(p-trimethylsilyl-α-methylstyrene). Other organic groups, which may be incorporated in the polymer backbone, may include acetylene terminated oligophenylenes, vinylbenzyl terminated aromatic polysulphones oligomers, aromatic polyesters, aromatic polyester based monomers, polyalkylenes, polyurethanes, aliphatic polyesters, aliphatic polyamides and aromatic polyamides.

Alternatively, the organic polymer blocks in a siloxane organic block copolymer for ingredient (B) may be polyoxyalkylene based blocks comprising recurring oxyalkylene units, illustrated by the average formula (—$C_gH_{2g}$—O—)$_h$ where subscript g is an integer with a value ranging from 2 to 4 and subscript h is an integer of at least four. The number average molecular weight (Mn) of each polyoxyalkylene polymer block may range from 300 to 10,000. Moreover, the oxyalkylene units are not necessarily identical throughout the polyoxyalkylene block, but can differ from unit to unit. A polyoxyalkylene block, for example, can comprise oxyethylene units (—$C_2H_4$—O—), oxypropylene units (—$C_3H_6$—O—) or oxybutylene units (—$O_4H_8$—O—), or combinations thereof. Alternatively, the polyoxyalkylene polymeric backbone may consist essentially of oxyethylene units and/or oxypropylene units. Other polyoxyalkylene blocks may include for example, units of the structure: —[—$R^5$—O—(—$R^6$—O—)$_i$—Pn-$CR^7_2$—Pn-O—(—$R^6$—O—)$_j$—$R^5$]—, in which Pn is a 1,4-phenylene group, each $R^5$ is the same or different and is a divalent hydrocarbon group having 2 to 8 carbon atoms, each $R^6$ is the same or different and is an ethylene group or propylene group, each $R^7$ is the same or different and is a hydrogen atom or methyl group and each of the subscripts i and j each represent a positive integer having a value ranging from 3 to 30.

Alternatively, ingredient (B) may comprise a silicone resin, in addition to, or instead of, one of the polymers described above for ingredient (B). Suitable silicone resins are exemplified by an MQ resin, which comprises siloxane units of the formulae: $R^{29}_w R^{30}_{(3-w)} SiO_{1/2}$ and $SiO_{4/2}$, where $R^{29}$ and $R^{30}$ are monovalent organic groups, such as monovalent hydrocarbon groups exemplified by alkyl such as methyl, ethyl, propyl, pentyl, octyl, decyl, dodecyl, undecyl, and octadecyl; alkenyl, such as vinyl, allyl, and hexenyl; cycloalkyl such as cyclopentyl and cyclohexyl; aryl such as phenyl, tolyl, xylyl, and benzyl; and aralkyl such as 1-phenylethyl or 2-phenylethyl; halogenated hydrocarbon group exemplified by chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl; and other monovalent organic groups such as hydrocarbon groups substituted with oxygen atoms such as glycidoxyalkyl, and hydrocarbon groups substituted with nitrogen atoms such as aminoalkyl and cyano-functional groups such as cyanoethyl and cyanopropyl; and each instance of subscript w is 0, 1, or 2. Alternatively, each $R^{29}$ and each $R^{30}$ may be an alkyl group. The MQ resin may have a molar ratio of M units to Q units (M:Q) ranging from 0.5:1 to 1.5:1. These mole ratios are conveniently measured by $Si^{29}NMR$ spectroscopy. This technique is capable of quantitatively determining the concentration of $R^{29}_3 SiO_{1/2}$ ("M") and $SiO_{4/2}$ ("Q") units derived from the silicone resin and from the neopentamer, $Si(OSiMe_3)_4$, present in the initial silicone resin, in addition to the total hydroxy content of the silicone resin.

The MQ silicone resin is soluble in solvents such as liquid hydrocarbons exemplified by benzene, toluene, xylene, and heptane, or in liquid organosilicon compounds such as a low viscosity cyclic and linear polydiorganosiloxanes.

The MQ silicone resin may contain 2.0% or less, alternatively 0.7% or less, alternatively 0.3% or less, of terminal units represented by the formula $X''SiO_{3/2}$, where $X''$ represents a hydroxy group. The concentration of silanol groups present in the silicone resin can be determined using FTIR.

The Mn desired to achieve the desired flow characteristics of the MQ silicone resin can depend at least in part on the Mn of the silicone resin and the type of organic group, represented by $R^{29}$, that are present in this ingredient. The Mn of the MQ silicone resin is typically greater than 3,000, more typically from 4500 to 7500.

The MQ silicone resin can be prepared by any suitable method. Silicone resins of this type have reportedly been prepared by cohydrolysis of the corresponding silanes or by silica hydrosol capping methods known in the art. Briefly stated, the method involves reacting a silica hydrosol under acidic conditions with a hydrolyzable triorganosilane such as trimethylchlorosilane, a siloxane such as hexamethyldisiloxane, or a combination thereof, and recovering a product comprising M and Q units (MQ resin). The resulting MQ resins may contain from 2 to 5 percent by weight of silicon-bonded hydroxy groups.

The intermediates used to prepare the MQ silicone resin may be triorganosilanes of the formula $R^{29}_3 SiX'$, where $X'$ represents a hydrolyzable group, such as halogen, alkoxy or hydroxy, and either a silane with four hydrolyzable groups such as halogen, alkoxy or hydroxy, or an alkali metal silicate such as sodium silicate.

Various suitable MQ resins are commercially available from sources such as Dow Corning Corporation of Midland, Mich., U.S.A., Momentive Performance Materials of Albany, N.Y., U.S.A., and Bluestar Silicones USA Corp. of East Brunswick, N.J., U.S.A. For example, DOW CORNING® MQ-1600 Solid Resin, DOW CORNING® MQ-1601 Solid Resin, and DOW CORNING® 1250 Surfactant, DOW CORNING® 7466 Resin, and DOW CORNING® 7366 Resin, all of which are commercially available from Dow Corning Corporation, are suitable for use in the methods described herein. Alternatively, a resin containing M, T, and Q units may be used, such as DOW CORNING® MQ-1640 Flake Resin, which is also commercially available from Dow Corning Corporation. Such resins may be supplied in organic solvent.

Alternatively, the silicone resin may comprise a silsesquioxane resin, i.e., a resin containing T units of formula $(R^{31}SiO_{3/2})$. Each $R^{31}$ may be independently selected from a hydrogen atom and a monovalent organic group, such as a monovalent hydrocarbon group exemplified by alkyl such as methyl, ethyl, propyl, pentyl, octyl, decyl, dodecyl, undecyl, and octadecyl; cycloalkyl such as cyclopentyl and cyclohexyl; aryl such as phenyl, tolyl, xylyl, and benzyl; and aralkyl such as 1-phenylethyl or 2-phenylethyl; halogenated hydrocarbon group exemplified by chlorinated alkyl groups such as chloromethyl and chloropropyl groups; a fluorinated alkyl group such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl; and another monovalent organic group such as a hydrocarbon group substituted with oxygen atoms such as glycidoxyalkyl, and a hydrocarbon group substituted with a nitrogen atom such as aminoalkyl and cyano-functional groups such as cyanoethyl and cyanopropyl.

Silsesquioxane resins suitable for use herein are known in the art and are commercially available. For example, a methylmethoxysiloxane methylsilsesquioxane resin having a DP of 15 and a weight average molecular weight (Mw) of 1200 g/mole is commercially available as DOW CORNING® US-CF 2403 Resin from Dow Corning Corporation of Midland, Mich., U.S.A. Alternatively, the silsesquioxane resin may have phenylsilsesquioxane units, methylsilsesquioxane units, or a combination thereof. Such resins are known in the art and are commercially available as DOW CORNING® 200 Flake resins, also available from Dow Corning Corporation. Alternatively, the silicone resin may comprise D units of formulae $(R^{31}_2SiO_{2/2})$ and/or $(R^{31}R^{32}SiO_{2/2})$ and T units of formulae $(R^{31}SiO_{3/2})$ and/or $(R^{32}SiO_{3/2})$, i.e., a DT resin, where $R^{31}$ is as described above and $R^{32}$ is a hydrolyzable group such as group X' described above. DT resins are known in the art and are commercially available, for example, methoxy functional DT resins include DOW CORNING® 3074 and DOW CORNING® 3037 resins; and silanol functional resins include DOW CORNING® 800 Series resins, which are also commercially available from Dow Corning Corporation. Other suitable resins include DT resins containing methyl and phenyl groups and/or resin-linear polymers.

Alternatively, ingredient (B) may comprise a resin-linear polymer. The resin-linear polymer is an organosiloxane block copolymer comprising:

40 to 90 mole percent disiloxy units of the formula $[R^{71}_2SiO_{2/2}]$, 10 to 60 mole percent trisiloxy units of the formula $[R^{72}SiO_{3/2}]$, 0.5 to 35 mole percent silanol groups [≡SiOH];

where:

each $R^{71}$ and $R^{72}$ is independently a hydrocarbon group having 1 to 30 carbon atoms or a halogenated hydrocarbon group having 1 to 30 carbon atoms;

where:

the disiloxy units $[R^{71}_2SiO_{2/2}]$ are arranged in linear blocks having an average of from 10 to 400 disiloxy units $[R^{71}_2SiO_{2/2}]$ per linear block, the trisiloxy units $[R^{72}SiO_{3/2}]$ are arranged in non-linear blocks having a molecular weight of at least 500 g/mole, and at least 30% of the non-linear blocks are crosslinked with each other.

each linear block is linked to at least one non-linear block; and the organosiloxane block copolymer has a weight average molecular weight ($M_w$) of at least 20,000 g/mole. As used herein "organosiloxane block copolymers" or "resin-linear organosiloxane block copolymers" refer to organopolysiloxanes containing "linear" D siloxy units in combination with "resin" T siloxy units. In some embodiments, the organosiloxane copolymers are "block" copolymers, as opposed to "random" copolymers. As such, the "resin-linear organosiloxane block copolymers" of the disclosed embodiments refer to organopolysiloxanes containing D and T siloxy units, where the D units (i.e., $[R^1_2SiO_{2/2}]$ units) are primarily bonded together to form polymeric chains having, in some embodiments, an average of from 10 to 400 D units (e.g., 10 to 400 D units; 10 to 300 D units; 10 to 200 D units; 10 to 100 D units; 50 to 400 D units; 100 to 400 D units; 150 to 400 D units; 200 to 400 D units; 300 to 400 D units; 50 to 300 D units; 100 to 300 D units; 150 to 300 D units; 200 to 300 D units; 100 to 150 D units, 115 to 125 D units, 90 to 170 D units or 110 to 140 D units), which are referred herein as "linear blocks".

The T units (i.e., $[R^{72}SiO_{3/2}]$) are primarily bonded to each other to form branched polymeric chains, which are referred to as "non-linear blocks". In some embodiments, a significant number of these non-linear blocks may further aggregate to form "nano-domains" when solid forms of the block copolymer are provided. In some embodiments, these nano-domains form a phase separate from a phase formed from linear blocks having D units, such that a resin-rich phase forms. In some embodiments, the disiloxy units $[R^{71}_2SiO_{2/2}]$ are arranged in linear blocks having an average of from 10 to 400 disiloxy units $[R^{71}_2SiO_{2/2}]$ per linear block (e.g., 10 to 400 D units; 10 to 300 D units; 10 to 200 D units; 10 to 100 D units; 50 to 400 D units; 100 to 400 D units; 150 to 400 D units; 200 to 400 D units; 300 to 400 D units; 50 to 300 D units; 100 to 300 D units; 150 to 300 D units; 200 to 300 D units; 100 to 150 D units, 115 to 125 D units, 90 to 170 D units or 110 to 140 D units), and the trisiloxy units $[R^{72}SiO_{3/2}]$ are arranged in non-linear blocks having a molecular weight of at least 500 g/mole and at least 30% of the non-linear blocks are crosslinked with each other.

In some embodiments, the non-linear blocks have a number average molecular weight of at least 500 g/mole, e.g., at least 1000 g/mole, at least 2000 g/mole, at least 3000 g/mole or at least 4000 g/mole; or have a molecular weight of from 500 g/mole to 4000 g/mole, from 500 g/mole to 3000 g/mole, from 500 g/mole to 2000 g/mole, from 500 g/mole to 1000 g/mole, from 1000 g/mole to 2000 g/mole, from 1000 g/mole to 1500 g/mole, from 1000 g/mole to 1200 g/mole, from 1000 g/mole to 3000 g/mole, from 1000 g/mole to 2500 g/mole, from 1000 g/mole to 4000 g/mole, from 2000 g/mole to 3000 g/mole or from 2000 g/mole to 4000 g/mole.

In some embodiments, at least 30% of the non-linear blocks are crosslinked with each other, e.g., at least 40% of the non-linear blocks are crosslinked with each other; at least 50% of the non-linear blocks are crosslinked with each other; at least 60% of the non-linear blocks are crosslinked with each other; at least 70% of the non-linear blocks are crosslinked with each other; or at least 80% of the non-linear blocks are crosslinked with each other. In other embodiments, from 30% to 80% of the non-linear blocks are crosslinked with each other; from 30% to 70% of the non-linear blocks are crosslinked with each other; from 30% to 60% of the non-linear blocks are crosslinked with each other; from 30% to 50% of the non-linear blocks are crosslinked with each other; from 30% to 40% of the non-linear blocks are crosslinked with each other; from 40% to 80% of the non-linear blocks are crosslinked with each other; from 40% to 70% of the non-linear blocks are crosslinked with each other; from 40% to 60% of the non-linear blocks are crosslinked with each other; from 40% to 50% of the non-linear blocks are crosslinked with each other; from 50% to 80% of the non-linear blocks are crosslinked with each other; from 50% to 70% of the non-linear blocks are crosslinked with each other; from 55% to 70% of the non-linear blocks are crosslinked with each other, from 50% to 60% of the non-linear blocks are crosslinked with each other; from 60% to 80% of the non-linear blocks are crosslinked with each other; or from 60% to 70% of the non-linear blocks are crosslinked with each other.

In some embodiments, the organosiloxane block copolymers of the embodiments described herein comprise 10 to 60 mole percent trisiloxy units of the formula $[R^{72}SiO_{3/2}]$, e.g., 10 to 20 mole percent trisiloxy units of the formula $[R^{72}SiO_{3/2}]$; 10 to 30 mole percent trisiloxy units of the formula $[R^{72}SiO_{3/2}]$; 10 to 35 mole percent trisiloxy units of the formula $[R^{72}SiO_{3/2}]$; 10 to 40 mole percent trisiloxy units of the formula $[R^{72}SiO_{3/2}]$; 10 to 50 mole percent trisiloxy units of the formula $[R^{72}SiO_{3/2}]$; 20 to 30 mole percent trisiloxy units of the formula $[R^{72}SiO_{3/2}]$; 20 to 35 mole percent trisiloxy units of the formula $[R^{72}SiO_{3/2}]$; 20 to 40 mole percent trisiloxy units of the formula $[R^{72}SiO_{3/2}]$; 20 to 50 mole percent trisiloxy units of the formula $[R^{72}SiO_{3/2}]$; 20 to 60 mole percent trisiloxy units of the formula $[R^{72}SiO_{3/2}]$; 30 to 40 mole percent trisiloxy units of the formula $[R^{72}SiO_{3/2}]$; 30 to 50 mole percent trisiloxy units of the formula $[R^{72}SiO_{3/2}]$; 30 to 60 mole percent trisiloxy units of the formula $[R^{72}SiO_{3/2}]$; 40 to 50 mole percent trisiloxy units of the formula $[R^{72}SiO_{3/2}]$; or 40 to 60 mole percent trisiloxy units of the formula $[R^{72}SiO_{3/2}]$. It should be understood that the organosiloxane block copolymers of the embodiments described herein may contain additional siloxy units, such as M siloxy units, Q siloxy units, other unique D or T siloxy units (for example having organic groups other than $R^{71}$ or $R^{72}$), provided that the organosiloxane block copolymer contains the mole fractions of the disiloxy and trisiloxy units as described above.

In one embodiment, the organosiloxane block copolymer consists essentially of the disiloxy units of the formula $[R^{71}_2SiO_{2/2}]$ and trisiloxy units of the formula $[R^{72}SiO_{3/2}]$, while also containing 0.5 to 25 mole percent silanol groups $[\equiv SiOH]$ (e.g., 0.5 to 5 mole percent, 0.5 to 10 mole percent, 0.5 to 15 mole percent, 0.5 to 20 mole percent, 5 to 10 mole percent, 5 to 15 mole percent, 5 to 20 mole percent, 5 to 25 mole percent, 10 to 15 mole percent 10 to 20 mole percent, 10 to 25 mole percent, 15 to 20 mole percent, 15 to 25 mole percent, or 20 to 25 mole percent), where $R^{71}$ and $R^{72}$ are as defined above. Thus, in this embodiment, the sum of mole percents of the disiloxy units and the trisiloxy units is greater than 95 mole %, alternatively greater than 98 mole %. The amount of silanol groups present on the organosiloxane block copolymer may vary from 0.5 to 35 mole percent silanol groups $[\equiv SiOH]$, alternatively from 2 to 32 mole percent silanol groups $[\equiv SiOH]$, alternatively from 8 to 22 mole percent silanol groups $[\equiv SiOH]$. In other words, the sum of the mole percents for the disiloxy units and the trisiloxy units do not necessarily have to sum to 100. The sum may be less than 100 mole percent to account for amounts of silanol groups and other siloxy units that may be present in the organosiloxane block copolymer. Alternatively, the sum is greater than 60 mole %, alternatively greater than 70 mol %, alternatively greater than 80 mol %, or alternatively greater than 90 mol %. In some embodiments, the sum of a+b is from 60 mol % to 90 mol %, e.g., from 60 mol % to 80 mol %, alternatively 60 mol % to 70 mol %, alternatively 70 mol % to 90 mol %, alternatively 70 mol % to 80 mol %, and alternatively 70 mol % to 90 mol %

The silanol groups may be present on any siloxy units within the organosiloxane block copolymer. The amount described above represent the total amount of silanol groups found in the organosiloxane block copolymer. In some embodiments, the majority (e.g., greater than 75 mol %, greater than 80 mol %, greater than 90 mol %; from 75 mol % to 90 mol %, from 80 mol % to 90 mol %, or from 75 mol % to 85 mol %) of the silanol groups will reside on the trisiloxy units, i.e., the resin component of the block copolymer. Although not wishing to be bound by any theory, the silanol groups present on the resin component of the organosiloxane block copolymer allows for the block copolymer to further react or cure at elevated temperatures.

Each $R^{71}$ and $R^{72}$ in the above unit formulae is a monovalent organic group selected from a hydrocarbon group of 1 to 30 carbon atoms or a halogenated hydrocarbon group of 1 to 30 carbon atoms. Alternatively, the group selected for $R^{71}$ and/or $R^{72}$ may have 1 to 18 carbon atoms, alternatively 1 to 6 carbon atoms, and alternatively 1 to 4 carbon atoms. Examples of suitable hydrocarbon groups and halogenated hydrocarbon groups are as described above for $R^2$. Alternatively $R^{71}$ may be an alkyl group such as Me, Et, Pr, Bu, pentyl, or hexyl. Alternatively $R^{71}$ may be methyl. $R^{71}$ may be an aryl group, such as phenyl, naphthyl, or an anthryl group. Alternatively, $R^{71}$ may be any combination of the aforementioned alkyl or aryl groups. Alternatively, $R^{71}$ is phenyl, methyl, or a combination of both. $R^{72}$ may be an aryl group, such as phenyl, naphthyl, or anthryl. Alternatively, $R^{72}$ may be an alkyl group, such as methyl, ethyl, propyl, or butyl. Alternatively, $R^{72}$ may be any combination of the aforementioned alkyl or aryl groups. Alternatively, $R^{72}$ is phenyl or methyl. Alternatively, $R^{72}$ may be an aryl group such as phenyl. Alternatively, one of $R^{71}$ may be aryl such as phenyl and the other of $R^{71}$ may be alkyl such as methyl.

The organosiloxane block copolymers described herein have a Mw of at least 20,000 g/mole, alternatively Mw of at least 40,000 g/mole, alternatively a Mw of at least 50,000 g/mole, alternatively a Mw of at least 60,000 g/mole, alternatively a Mw of at least 70,000 g/mole, or alternatively a Mw of at least 80,000 g/mole. In some embodiments, the organosiloxane block copolymers of the embodiments described herein have a Mw of from 20,000 g/mole to 250,000 g/mole or from 100,000 g/mole to 250,000 g/mole, alternatively a Mw of from 40,000 g/mole to 100,000 g/mole, alternatively a Mw of from 50,000 g/mole to 100,000 g/mole, alternatively a Mw of from 50,000 g/mole to 80,000 g/mole, alternatively a Mw of from 50,000 g/mole to 70,000 g/mole, alternatively a Mw of from 50,000 g/mole to 60,000 g/mole. The average molecular weight may be readily determined using Gel Permeation Chromatography (GPC) techniques. In some embodiments, the organosiloxane block copolymers of the embodiments described herein have a $M_n$ of 15,000 to 50,000 g/mole; alternatively 15,000 to 30,000 g/mole; alternatively from 20,000 to 30,000 g/mole; or alternatively from 20,000 to 25,000 g/mole.

In some embodiments, the structural ordering of the disiloxy and trisiloxy units in the resin-linear copolymer may be further described as follows: the disiloxy units $[R^{71}_2SiO_{2/2}]$ are arranged in linear blocks having an average of from 10 to 400 disiloxy units $[R^{71}_2SiO_{2/2}]$ per linear block, and the trisiloxy units $[R^{72}SiO_{3/2}]$ are arranged in non-linear blocks having a molecular weight of at least 500 g/mole. Each linear block is linked to at least one non-linear block in the block copolymer. Furthermore, at least 30% of the non-linear blocks are crosslinked with each other, alternatively at least at 40% of the non-linear blocks are crosslinked with each other, and alternatively at least at 50% of the non-linear blocks are crosslinked with each other.

In other embodiments, from 30% to 80% of the non-linear blocks are crosslinked with each other; from 30% to 70% of the non-linear blocks are crosslinked with each other; from 30% to 60% of the non-linear blocks are crosslinked with each other; from 30% to 50% of the non-linear blocks are crosslinked with each other; from 30% to 40% of the non-linear blocks are crosslinked with each other; from 40% to 80% of the non-linear blocks are crosslinked with each other; from 40% to 70% of the non-linear blocks are crosslinked with each other; from 40% to 60% of the non-linear blocks are crosslinked with each other; from 40% to 50% of the non-linear blocks are crosslinked with each other; from 50% to 80% of the non-linear blocks are crosslinked with each other; from 50% to 70% of the non-linear blocks are crosslinked with each other; from 50% to 60% of the non-linear blocks are crosslinked with each other; from 60% to 80% of the non-linear blocks are crosslinked with each other; or from 60% to 70% of the non-linear blocks are crosslinked with each other.

The crosslinking of the non-linear blocks may be accomplished via a variety of chemical mechanisms and/or moieties. For example, crosslinking of non-linear blocks within the block copolymer may result from the condensation of residual silanol groups present in the non-linear blocks of the copolymer. Crosslinking of the non-linear blocks within the block copolymer may also occur between "free resin" components and the non-linear blocks. "Free resin" components may be present in the block copolymer compositions as a result of using an excess amount of an organosiloxane resin during the preparation of the block copolymer. The free resin component may crosslink with the non-linear blocks by condensation of the residual silanol groups present on the non-blocks and on the free resin. The free resin may provide crosslinking by reacting with lower molecular weight compounds added as crosslinkers, as described below. The free resin, when present, may be present in an amount of from 10% to 20% by weight of the organosiloxane block copolymers of the embodiments described herein, e.g., from 15% to 20% by weight organosiloxane block copolymers of the embodiments described herein.

Alternatively, a crosslinker may be added during the preparation of the block copolymer to specifically crosslink the non-resin blocks. The crosslinker may be a crosslinker described below for ingredient (C). Alternatively, the crosslinker may include an organosilane having the formula $R^{75}_qSiX_{4-q}$, which is added during the formation of the block copolymer, where $R^5$ is a hydrocarbon group or a halogenated hydrocarbon group of 1 to 8 carbon atoms; X is a hydrolyzable moiety; and subscript q is 0, 1, or 2. Alternatively $R^{75}$ is an alkyl group, or alternatively a phenyl group, or alternatively $R^{75}$ is methyl, ethyl, or a combination of methyl and ethyl. X is any hydrolyzable group, alternatively X may be an oximo, acetoxy, halogen atom, hydroxy (OH), or an alkoxy group.

In one embodiment, the organosilane having the formula $R^{75}_qSiX_{4-q}$ is an alkyltriacetoxysilane, such as methyltriacetoxysilane, ethyltriacetoxysilane, or a combination of both. Commercially available representative alkyltriacetoxysilanes include ETS-900 (Dow Corning Corp., Midland, Mich.).

Other suitable, non-limiting organosilanes useful as crosslinkers include; methyl-tris(methylethylketoxime)silane (MTO), methyl triacetoxysilane, ethyl triacetoxysilane, tetraacetoxysilane, tetraoximesilane, dimethyl diacetoxysilane, dimethyl dioximesilane, methyl tris(methylmethylketoxime)silane.

The crosslinks within the block copolymer will primarily be siloxane bonds, ≡Si—O—Si≡, resulting from the condensation of silanol groups, as discussed above.

The amount of crosslinking in the block copolymer may be estimated by determining the average molecular weight of the block copolymer, such as with GPC techniques. Typically, crosslinking the block copolymer increases its average molecular weight. Thus, an estimation of the extent of crosslinking may be made, given the average molecular weight of the block copolymer, the selection of the linear siloxy component (that is the chain length as indicated by its degree of polymerization), and the molecular weight of the non-linear block (which is primarily controlled by the selection of the selection of the organosiloxane resin used to prepare the block copolymer).

The organosiloxane block copolymer (resin-linear polymer) may be prepared by the methods known in the art, including the methods disclosed in U.S. Pat. Nos. 8,921,493; 9,006,356 and 9,006,358 and Published PCT Application Nos. WO2012/040302 and WO2012/040305, which are incorporated herein by reference in their entirety.

The amount of silicone resin added to the composition can vary depending on the end use of the composition. For example, when the reaction product of the composition is a gel, little or no silicone resin may be added. However, the amount of silicone resin in the composition may range from 0% to 90%, alternatively 0.1% to 50%, based on the weight of all ingredients in the composition.

The amount of ingredient (B) can depend on various factors including the end use of the reaction product of the composition, the type of Si—OH functional compound selected for ingredient (B), and the type(s) and amount(s) of any additional ingredient(s) present, if any. However, the amount of ingredient (B) may range from 0.01% to 99%, alternatively 10% to 95%, alternatively 10% to 65% of the composition.

Ingredient (B) can be one single Si—OH functional compound or a combination comprising two or more Si—OH functional compounds that differ in at least one of the following properties: average molecular weight, hydrolyzable substituents, siloxane units, sequence, and viscosity.

In one embodiment, ingredient (C) is added to the composition described above. Ingredient (C) is a crosslinker that may be added to the composition, for example, to increase crosslink density of the reaction product prepared by condensation reaction of the composition. Generally, ingredient (C) is selected with functionality that can vary depending on the degree of crosslinking desired in the reaction product of the composition and such that the reaction product does not exhibit too much weight loss from by-products of the condensation reaction. Generally, the selection of ingredient (C) is made such that the composition remains sufficiently reactable to be useful during storage for several months in a moisture impermeable package. Generally, ingredient (C) is selected such that the hydrolyzable substituents on ingredient (C) are reactive with the hydroxy groups on ingredient (B). For example, the hydrolyzable substituent for ingredient (C) may be a hydrogen atom, a halogen atom; an amido group, an acyloxy groups, a hydrocarbonoxy group, an amino group, an aminoxy group, a mercapto group, an oximo group, a ketoximo group, or an alkoxysilylhydrocarbylene group, or a combination thereof. The exact amount of ingredient (C) can vary depending on factors including the type of hydroxy-functional compound for (B) and crosslinker (C) selected, the reactivity of the hydroxy groups on ingredient (B) and reactivity of crosslinker (C), and the desired crosslink density of the reaction product. However, the amount of crosslinker may range from 0.5 to 100 parts based on 100 parts by weight of ingredient (B).

Ingredient (C) may comprise a silane crosslinker having hydrolyzable groups or partial or full hydrolysis products thereof. Ingredient (C) has an average, per molecule, of greater than two substituents reactive with the hydroxy groups on ingredient (B). Examples of suitable silane crosslinkers for ingredient (C) may have the general formula: $R^8_k Si(R^9)_{(4-k)}$, where each $R^8$ is independently a monovalent hydrocarbon group such as an alkyl group; each $R^9$ is a hydrolyzable substituent, which may be hydroxy as described above for ingredient (B). Alternatively, each $R^9$ may be, for example, a hydrogen atom, a halogen atom, an acetamido group, an acyloxy group such as acetoxy, an alkoxy group, an amido group, an amino group, an aminoxy group, a hydroxy group, an oximo group, a ketoximo group, or a methylacetamido group; and each instance of subscript k may be 0, 1, or 2. For ingredient (C), subscript k has an average value less than 2. Alternatively, subscript k may have a value ranging from 0 to 1. Alternatively, each $R^9$ may be independently selected from hydroxy, alkoxy, acyloxy such as acetoxy, amide, or oxime. Alternatively, ingredient (C) may be selected from an acyloxysilane, an alkoxysilane, a ketoximosilane, and an oximosilane.

Ingredient (C) may comprise an alkoxysilane exemplified by a dialkoxysilane, such as a dialkyldialkoxysilane; a trialkoxysilane, such as an alkyltrialkoxysilane; a tetraalkoxysilane; or partial or full hydrolysis products thereof, or another combination thereof. Examples of suitable trialkoxysilanes include methyltrimethoxysilane, methyltriethoxysilane, ethyltrimethoxysilane, ethyltriethoxysilane, isobutyltrimethoxysilane, isobutyltriethoxysilane, and a combination thereof, and alternatively methyltrimethoxysilane. Examples of suitable tetraalkoxysilanes include tetraethoxysilane. The amount of the alkoxysilane that is used in the curable silicone composition may range from 0.5 to 15, parts by weight per 100 parts by weight of ingredient (B1).

Alternatively, ingredient (C) may comprise an acyloxysilane, such as an acetoxysilane, e.g., methyltriacetoxysilane, ethyltriacetoxysilane, and combinations thereof. Alternatively, ingredient (C) may comprise a silane containing both alkoxy and acetoxy groups, e.g., methyldiacetoxymethoxysilane, methylacetoxydimethoxysilane, vinyldiacetoxymethoxysilane, vinylacetoxydimethoxysilane, methyldiacetoxyethoxysilane, metylacetoxydiethoxysilane, and combinations thereof. Alternatively, ingredient (C) may comprise an aminofunctional alkoxysilane. Alternatively, ingredient (C) may comprise an oximosilane and/or a ketoximosilane. Alternatively, ingredient (C) may be polymeric. For example, ingredient (C) may comprise a disilane such as bis(triethoxysilyl)hexane), 1,4-bis[trimethoxysilyl (ethyl)]benzene, and bis[3-(triethoxysilyl)propyl] tetrasulfide.

Alternatively, ingredient (C) may comprise a Si—H functional compound, i.e., a compound having an average, per molecule, of one or more silicon bonded hydrogen moieties. Alternatively, ingredient (C) may have 2 or more Si—H moieties. Ingredient (C) may comprise a silane and/or a polyorganohydrogensiloxane. The Si—H moiety in a polyorganohydrogensiloxane for ingredient (C) may be located at terminal, pendant, or both terminal and pendant positions in the polymer. Polyorganohydrogensiloxanes for ingredient (C) may comprise linear, branched, cyclic, or resinous structures. Alternatively, ingredient (C) may comprise a linear, branched or cyclic structure. Alternatively, ingredient (C) may comprise a linear or branched structure. Alternatively, ingredient (C) may comprise a linear structure. Alternatively, ingredient (C) may comprise a linear structure and a resinous structure. Ingredient (C) may comprise a homopolymer or a copolymer or a combination thereof.

Ingredient (C) may comprise a silane of formula $R^{51}_{bb}SiH_{cc}$, where subscript bb is 0, 1, 2, or 3; and subscript cc is 1, 2, 3, or 4, with the proviso that a sum of (bb+cc) is 4. Each $R^{51}$ is independently a halogen atom or a monovalent organic group. Suitable halogen atoms for $R^{51}$ are exemplified by chlorine, fluorine, bromine, and iodine; alternatively chlorine. Suitable monovalent organic groups for $R^{51}$ include, but are not limited to, monovalent hydrocarbon and monovalent halogenated hydrocarbon groups. Monovalent hydrocarbon groups include, but are not limited to, alkyl such Me, Et, Pr, Bu, pentyl, hexyl, heptyl, octyl, decyl, dodecyl, undecyl, and octadecyl; cycloalkyl such as cyclopentyl and cyclohexyl; aryl such as Ph, tolyl, xylyl, naphthyl, and benzyl; and aralkyl such as 1-phenylethyl and 2-phenylethyl. Examples of monovalent halogenated hydrocarbon groups include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5, 4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups include, but are not limited to, hydrocarbon groups substituted with oxygen atoms such as glycidoxyalkyl, and alkoxy groups such as methoxy, ethoxy, propoxy, and butoxy; and hydrocarbon groups substituted with nitrogen atoms such as aminoalkyl and cyano-functional groups such as cyanoethyl and cyanopropyl. Examples of suitable Si—H functional silanes for ingredient (C) are exemplified by trichlorosilane ($HSiCl_3$), $Me_2HSiCl$, or $MeHSi(OMe)_2$.

Alternatively, ingredient (C) may be a polyorganohydrogensiloxane. The polyorganohydrogensiloxane may have a linear structure. When ingredient (C) is linear, ingredient (C) may comprise a hydrido-endblocked polydiorganosiloxane, an hydridosilylhydrocarbylene-endblocked polydiorganosiloxane, or a combination thereof.

Ingredient (C) may comprise a polyorganohydrogensiloxane of unit formula (ii):

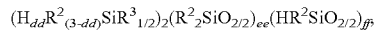

Where each $R^2$ is independently a monovalent organic group, each $R^3$ is independently an oxygen atom or a divalent hydrocarbon group, each subscript dd is independently 0, 1, 2, or 3, ee is ≥0, ff≥0, and a quantity (ee+ff) is an integer having a value sufficient to provide the polydiorganosiloxane with a viscosity of at least 5 mPa·s at 25° C. and/or a DP of at least 1, and with the proviso that at least one of dd and ff is greater than 0. DP may be measured by GPC using polystyrene standards calibration. Alternatively, subscript ee may have a value ranging from 1 to 200,000.

Suitable organic groups for $R^2$ include, but are not limited to, monovalent organic groups such as hydrocarbon groups and halogenated hydrocarbon groups. Examples of monovalent hydrocarbon groups for $R^2$ include, but are not limited to, alkyl such as methyl, ethyl, propyl, pentyl, octyl, decyl, dodecyl, undecyl, and octadecyl; cycloalkyl such as cyclopentyl and cyclohexyl; aryl such as phenyl, tolyl, xylyl, and benzyl; and aralkyl such as 1-phenylethyl and 2-phenylethyl. Examples of monovalent halogenated hydrocarbon groups for $R^2$ include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups for $R^2$ include, but are not limited to, hydrocarbon groups substituted with oxygen atoms such as glycidoxyalkyl, and hydrocarbon groups substituted with nitrogen atoms such as aminoalkyl and cyano-functional groups such as cyanoethyl and cyanopropyl. Alternatively, each $R^2$ may be an alkyl group such as methyl.

Ingredient (C) may comprise an α,ω-hydrido-polydiorganosiloxane when, in formula (ii) above, each subscript dd is 1, subscript ff is 0, and each $R^3$ is an oxygen atom. For example, ingredient (C) may have formula (iii): $HR^2_2SiO$—$(R^2_2SiO)_{ee'}$—$SiR^2_2H$, where $R^2$ is as described above and subscript ee' is an integer having a value sufficient to give the polydiorganosiloxane of formula (iii) the viscosity described above. Alternatively, subscript ee' may have a value ranging from 1 to 200,000, alternatively 50 to 1,000, and alternatively 200 to 700.

Alternatively, in formula (iii) described above, each $R^2$ may be an alkyl group such as methyl, and subscript ee' may have a value such that the Si—H functional polydiorganosiloxane has a viscosity of at least 100 mPa·s at 25° C. Alternatively, subscript e' may have a value ranging from 50 to 700. Exemplary Si—H-endblocked polydiorganosiloxanes are hydrido-endblocked polydimethylsiloxanes. Hydrido-endblocked polydiorganosiloxanes suitable for use as ingredient (C) may be prepared by methods known in the art, such as hydrolysis and condensation of the corresponding organohalosilanes or equilibration of cyclic polydiorganosiloxanes.

Ingredient (C) can be one single Si—H functional compound or a combination comprising two or more Si—H functional compounds that differ in at least one of the following properties: average molecular weight, hydrolyzable substituents, siloxane units, sequence, and viscosity.

Ingredient (C) can be one single crosslinker or a combination comprising two or more crosslinkers that differ from one another. Examples of suitable crosslinkers for ingredient (C) are exemplified by those described, for example, in PCT Publication No. WO2013/009836. Alternatively, the crosslinker may be selected from an alkoxysilane, such as methyltrimethoxysilane, ethyltrimethoxysilane, ethyltriethoxysilane, and a combination thereof, and a polyorganohydrogensiloxane such as an α,ω-hydrido-polydiorganosiloxane exemplified by hydrido-endblocked polydimethylsiloxane.

In an alternative embodiment, ingredient (F) is added to the composition comprising ingredients (A) and (B) described above. Ingredient (F) is a filler. The filler may comprise a reinforcing filler, an extending filler, a conductive filler, a phosphor, or a combination thereof. For example, the reinforcing filler, when present, may be added in an amount ranging from 0.1% to 95%, alternatively 1% to 60%, based on the weight of the composition. The exact amount of reinforcing filler depends on various factors including the form of the reaction product of the composition and whether any other fillers are added. Examples of suitable reinforcing fillers include reinforcing silica fillers such as fume silica, silica aerogel, silica xerogel, and precipitated silica. Fumed silicas are known in the art and commercially available.

The extending filler, when present, may be present in an amount ranging from 0.1% to 95%, alternatively 1% to 60%, and alternatively 1% to 20%, based on the weight of the composition. Examples of extending fillers include crushed quartz, aluminum oxide, magnesium oxide, calcium carbonate such as precipitated calcium carbonate, zinc oxide, talc, diatomaceous earth, iron oxide, clays, mica, chalk, titanium dioxide, zirconia, sand, carbon black, graphite, or a combination thereof. Extending fillers are known in the art and commercially available.

Conductive fillers may be thermally conductive, electrically conductive, or both. Conductive fillers are known in the art and are exemplified by metal particulates (such as aluminum, copper, gold, nickel, silver, and combinations thereof); such metals coated on nonconductive substrates; metal oxides (such as aluminum oxide, beryllium oxide, magnesium oxide, zinc oxide, and combinations thereof), meltable fillers (e.g., solder), aluminum nitride, aluminum trihydrate, barium titanate, boron nitride, carbon fibers, diamond, graphite, magnesium hydroxide, onyx, silicon carbide, tungsten carbide, and a combination thereof. The conductive filler, when present, may be present in an amount up to 80 vol % of the composition.

The phosphor includes, but is not limited to, aluminate phosphors (GAL), red nitride phosphors, garnet phosphors (NYAG), doped garnet phosphors such as YAG:Ce and (Y,Gd)AG:Ce; aluminates such as $Sr_2Al_{14}O_{25}$:Eu, and BAM:Eu; silicates such as SrBaSiO:Eu; sulfides such as ZnS:Ag, CaS:Eu, and $SrGa_2S4$:Eu; oxy-sulfides; oxy-nitrides; phosphates; borates; and tungstates such as $CaWO_4$. Other suitable phosphors include quantum dot phosphors made of semiconductor nanoparticles including, but not limited to Ge, CdS, CdSe, CdTe, ZnS, ZnSe, ZnTe, PbS, PbSe, PbTe, InN, InP, InAs, AlN, AlP, AlAs, GaN, GaP, GaAs and combinations thereof. Generally, a surface of each quantum dot phosphor will be at least partially coated with an organic molecule to prevent agglomeration and increase compatibility. In certain embodiments, the phosphor, e.g. quantum dot phosphor, is made up of several layers of different materials in a core-shell construction. Suitable organic molecules for coating the surface of the quantum dot phosphor include, but are not limited to, absorbing dyes and fluorescent dyes, such as those described in U.S. Pat. No. 6,600,175. Other suitable phosphors for purposes of the present invention are described in U.S. Patent Application Publication No. 2014/0008697, International Publication No. WO 2006/0600141 to Taskar et al., International Publication No. WO 2005/027576 to Taskar et al., U.S. Pat. No. 6,734,465 to Taskar et al., and U.S. Pat. No. 7,259,400 to Taskar at al., the disclosures of which pertaining to phosphors are incorporated herein by reference in their entirety. Phosphors are commercially available, for example, such as those described at http://www.intematix.com/products/led-phosphors, which are available from Intematix of Fremont, Calif., USA at http://www.intematix.com/products/chromalit.

If employed, phosphor used depends on various factors including the phosphor selected and the end use application. The phosphor, when present, may be added to the composition in an amount up to 80% by weight of the composition, alternatively 50% to 70%, alternatively 0.1% to 75%, and alternatively 5% to 70% by weight of the composition. When employed, the phosphor may be treated with (G) a treating agent, or untreated. Alternatively, the phosphor may be untreated.

Alternatively, other fillers may be added to the composition, the type and amount depending on factors including the end use of the cured product of the composition. Examples of such other fillers include magnetic particles such as ferrite; and dielectric particles such as fused glass microspheres, titania, and calcium carbonate. Examples of suitable fillers for ingredient (F) are exemplified by those described, for example, in PCT Publication No. WO2013/009836.

The composition may optionally further comprise ingredient (G) a treating agent. The amount of ingredient (G) can vary depending on factors such as the type of treating agent selected and the type and amount of particulates to be treated, and whether the particulates are treated before being added to the composition, or whether the particulates are treated in situ. However, ingredient (G) may be used in an amount ranging from 0.01% to 20%, alternatively 0.1% to 15%, and alternatively 0.5% to 5%, based on the weight of the composition. Particulates, such as the filler, the physical drying agent, certain flame retardants, certain pigments, and/or certain water release agents, when present, may optionally be surface treated with ingredient (G). Particulates may be treated with ingredient (G) before being added to the composition, or in situ. Ingredient (G) may comprise an alkoxysilane, an alkoxy-functional oligosiloxane, a cyclic polyorganosiloxane, a hydroxy-functional oligosiloxane such as a dimethyl siloxane or methyl phenyl siloxane, or a fatty acid. Examples of fatty acids include stearates such as calcium stearate.

Some representative organosilicon filler treating agents that can be used as ingredient (G) include compositions normally used to treat silica fillers such as organochlorosilanes, organosiloxanes, organodisilazanes such as hexaalkyl disilazane, and organoalkoxysilanes such as $C_6H_{13}Si(OCH_3)_3$, $C_8H_{17}Si(OC_2H_5)_3$, $C_{10}H_{21}Si(OCH_3)_3$, $C_{12}H_{25}Si(OCH_3)_3$, $C_{14}H_{29}Si(OC_2H_5)_3$, and $C_6H_5CH_2CH_2Si(OCH_3)_3$. Other treating agents that can be used include alkylthiols, fatty acids, titanates, titanate coupling agents, zirconate coupling agents, and combinations thereof.

Alternatively, ingredient (G) may comprise an alkoxysilane having the formula: $R^{13}{}_pSi(OR^{14})_{(4-p)}$, where subscript p may have a value ranging from 1 to 3, alternatively subscript p is 3. Each $R^{13}$ is independently a monovalent organic group, such as a monovalent hydrocarbon group of 1 to 50 carbon atoms, alternatively 8 to 30 carbon atoms, alternatively 8 to 18 carbon atoms. $R^{13}$ is exemplified by alkyl groups such as hexyl, octyl, dodecyl, tetradecyl, hexadecyl, and octadecyl; and aromatic groups such as benzyl and phenylethyl. $R^{13}$ may be saturated or unsaturated, and branched or unbranched. Alternatively, $R^{13}$ may be saturated and unbranched.

Each $R^{14}$ is independently a saturated hydrocarbon group of 1 to 4 carbon atoms, alternatively 1 to 2 carbon atoms. Ingredient (G) is exemplified by hexyltrimethoxysilane, octyltriethoxysilane, decyltrimethoxysilane, dodecyltrimethoxysilane, tetradecyltrimethoxysilane, phenylethyltrimethoxysilane, octadecyltrimethoxysilane, octadecyltriethoxysilane, and combinations thereof.

Alkoxy-functional oligosiloxanes may also be used as treating agents. For example, suitable alkoxy-functional oligosiloxanes include those of the formula $(R^{15}O)_qSi(OSiR^{16}{}_2R^{17})_{(4-q)}$. In this formula, subscript q is 1, 2 or 3, alternatively subscript q is 3. Each $R^{15}$ may be an alkyl group. Each $R^{16}$ may be an unsaturated monovalent hydrocarbon group of 1 to 10 carbon atoms. Each $R^{17}$ may be an unsaturated monovalent hydrocarbon group having at least 10 carbon atoms.

Certain particulates, such as metal fillers may be treated with alkylthiols such as octadecyl mercaptan; fatty acids such as oleic acid and stearic acid; and a combination thereof.

Other treating agents include alkenyl functional polyorganosiloxanes. Suitable alkenyl functional polyorganosiloxanes include, but are not limited to:

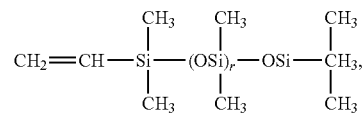

where subscript r has a value up to 1,500.

Examples of suitable treating agents for ingredient (G) are exemplified by those described, for example, in PCT Publication No. WO2013/009836.

Ingredient (S)

A vehicle (e.g., a solvent and/or diluent) may be used in the composition. Vehicle may facilitate flow of the composition and introduction of certain ingredients, such as silicone resin. Vehicles used herein are those that help fluidize the ingredients of the composition but essentially do not react with any of these ingredients. Vehicle may be selected based on solubility the ingredients in the composition and volatility. The solubility refers to the vehicle being sufficient to dissolve and/or disperse ingredients of the composition. Volatility refers to vapor pressure of the vehicle. If the vehicle is too volatile (having too high vapor pressure) bubbles may form in the composition at the application temperature, and the bubbles may cause cracks or otherwise weaken or detrimentally affect properties of the cured product. However, if the vehicle is not volatile enough (too low vapor pressure) the vehicle may remain as a plasticizer in the reaction product of the composition, or the amount of time for the reaction product to develop physical properties may be longer than desired.

Suitable vehicles include polyorganosiloxanes with suitable vapor pressures, such as hexamethyldisiloxane, octamethyltrisiloxane, hexamethylcyclotrisiloxane, and other low molecular weight polyorganosiloxanes, such as 0.5 to 1.5 centiStoke (cSt) Dow Corning® 200 Fluids and DOW CORNING® OS FLUIDS, which are commercially available from Dow Corning Corporation of Midland, Mich., U.S.A.

Alternatively, the vehicle may be an organic solvent. The organic solvent can be an alcohol such as methanol, ethanol, isopropanol, butanol, or n-propanol; a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride; chloroform; dimethyl sulfoxide; dimethyl formamide, acetonitrile; tetrahydrofuran; white spirits; mineral spirits; naphtha; n-methyl pyrrolidone; or a combination thereof.

The amount of vehicle can depend on various factors including the type of vehicle selected and the amount and type of other ingredients selected for the composition. However, the amount of vehicle may range from 1% to 99%, alternatively 2% to 50%, based on the weight of the composition.

When selecting ingredients for the composition described above, there may be overlap between types of ingredients because certain ingredients described herein may have more than one function. For example, certain alkoxysilanes may be useful as filler treating agents, crosslinkers, and/or adhesion promoters, certain fatty acid esters may be useful as plasticizers and may also be useful as filler treating agents, carbon black may be useful as a pigment, a flame retardant, and/or a filler, and nonreactive polydiorganosiloxanes such as polydimethylsiloxanes may be useful as extenders and as solvents.

The composition described above may be prepared as a one part composition, for example, by combining all ingredients by any convenient means, such as mixing. For example, a one-part composition may be made by optionally combining (e.g., premixing) the Si—OH-functional compound (B), and an extender (E) and mixing the resulting extended base polymer with all or part of the filler (F), and mixing this with a pre-mix comprising the crosslinker (C) and ingredient (A). Other additives such as (O) the anti-aging additive and (Q) the pigment may be added to the mixture at any desired stage. A final mixing step may be performed under substantially anhydrous conditions, and the resulting compositions are generally stored under substantially anhydrous conditions, for example in sealed containers, until ready for use.

Alternatively, the composition may be prepared as a multiple part (e.g., 2 part) composition when a crosslinker is present. In this instance the catalyst and crosslinker are stored in separate parts, and the parts are combined shortly before use of the composition. For example, a two part curable composition may be prepared by combining ingredients comprising (B) and (C) to form a first (curing agent) part by any convenient means such as mixing. A second (base) part may be prepared by combining ingredients comprising (A) and (B) by any convenient means such as mixing. The ingredients may be combined at ambient or elevated temperature and under ambient or anhydrous conditions, depending on various factors including whether a one part or multiple part composition is selected. The base part and curing agent part may be combined by any convenient means, such as mixing, shortly before use. The base part and curing agent part may be combined in relative amounts of base:curing agent ranging from 1:1 to 10:1.

The equipment used for mixing the ingredients is not specifically restricted. Examples of suitable mixing equipment may be selected depending on the type and amount of each ingredient selected. For example, agitated batch kettles may be used for relatively low viscosity compositions, such as compositions that would react to form gums or gels. Alternatively, continuous compounding equipment, e.g., extruders such as twin screw extruders, may be used for more viscous compositions and compositions containing relatively high amounts of particulates. Exemplary methods that can be used to prepare the compositions described herein include those disclosed in, for example, U.S. Patent Publications US 2009/0291238 and US 2008/0300358.

These compositions made as described above may be stable when the stored in containers that protect the compositions from exposure to moisture, but these compositions may react via condensation reaction when exposed to atmospheric moisture. Alternatively, when a low permeability composition is formulated, the composition may cure to form a cured product when moisture is released from a water release agent.

Compositions prepared as described above, and the reaction products thereof, have various uses. The ingredients described above may be used to prepare various types of composition comprising ingredients (A) and (B). The composition may further comprise one or more of the additional ingredients described above, depending on the type of composition and the desired end use of the composition and/or the reaction product of the composition. Alternatively, the ingredients and methods described above may be used to formulate curable compositions, for example, when ingredient (B) has two or more Si—OH moieties per molecule and/or a crosslinker is present in the composition. The compositions described herein may be reacted by condensation reaction by exposure to moisture. For example, the compositions may react via condensation reaction when exposed to atmospheric moisture. Alternatively, the composition react moisture is released from a water release agent, when a water release agent is present. Each composition described herein reacts to form a reaction product. The reaction product may have a form selected from a gum, a gel, a rubber, or a resin.

EXAMPLES

These examples are intended to illustrate some embodiments of the invention and should not be interpreted as limiting the scope of the invention set forth in the claims. Reference examples should not be deemed to be prior art unless so indicated. The following ingredients were used in the examples below. Anhydrous ingredients were used. The trans isomer is drawn for the M-NHC complexes numbered 1, 2, 3, 4, and 5, however, the isomer formed in the examples below may be cis, trans, or a mixture of both cis and trans isomers.

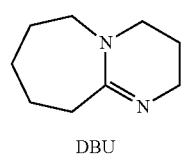

DBU

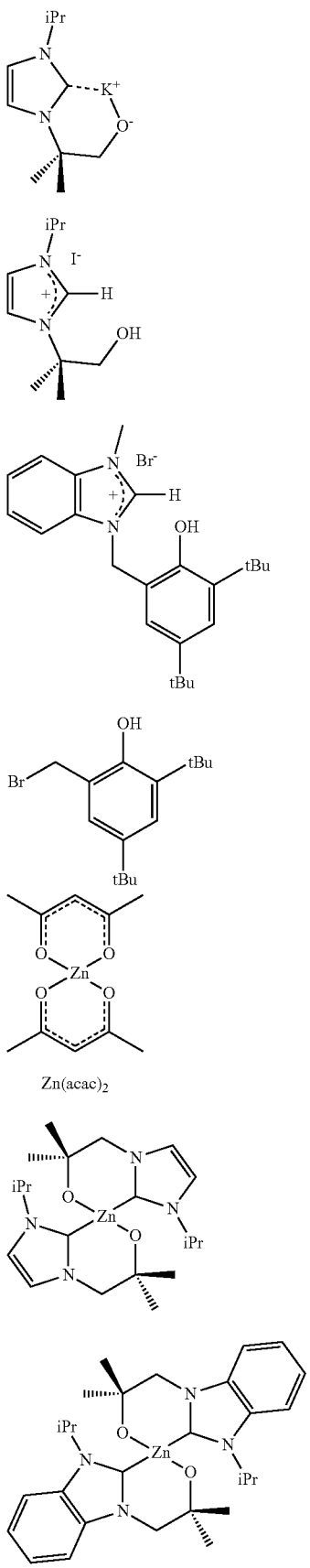

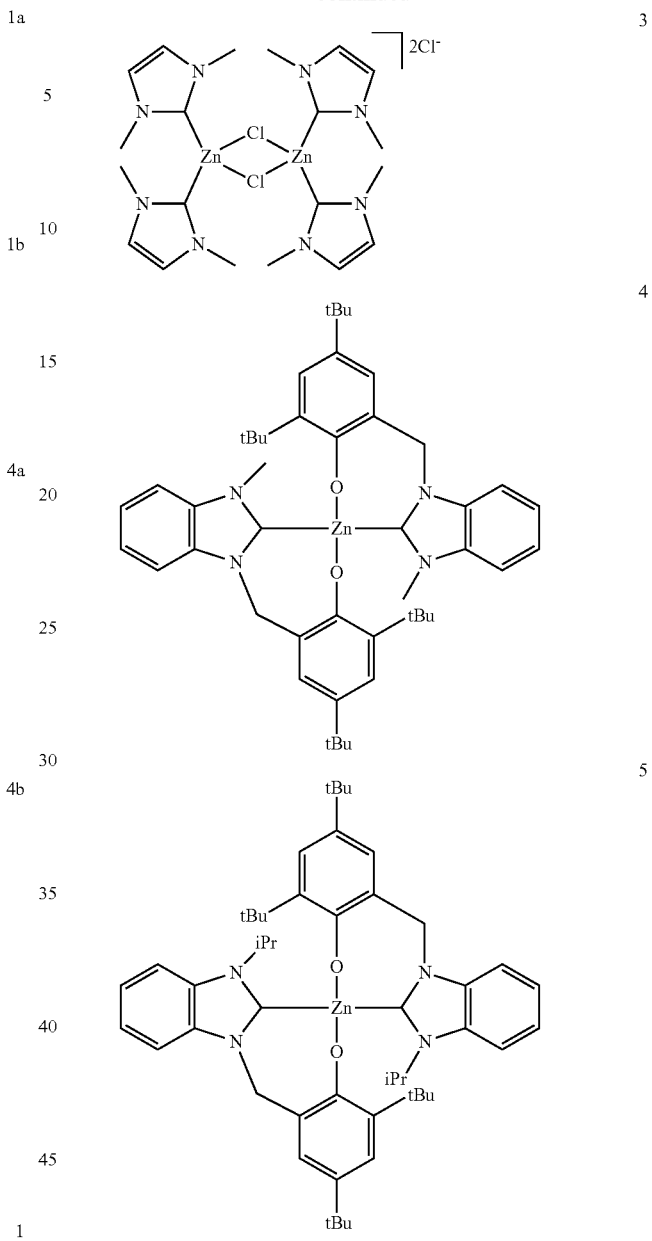

In example 1, curing of Ph-T-PhMe Resin Linear Copolymer at 150° C. in the absence of phosphor fillers was performed using the ingredients shown above as catalysts. The Ph-T-PhMe Resin Linear Copolymer was a hydroxy-functionalized, phenyl methyl siloxane/phenyl silsesquioxane block copolymer with 45% (PhSiO$_{3/2}$) units and an overall DP of 250 to 350. The results were measured on an ARES rheometer from (TA Instruments, USA), and the results are in Table 1. In Table 1, the cure profile for each sample was to increase temperature from 70° C. to 150° C. at 20° C. per minute. Tan delta=1 is a specific point at which the storage modulus equals the loss modulus. The time to reach Tan delta=1 was recorded in the table. >2700 s means tan delta equaled between 1 and 1.2 after 44 minutes, >>2700 s means tan delta equaled between 1.2 and 2, no cure means tan delta was greater than 2. The amount of Resin Linear Copolymer solids in each sample was 1.5 g.

TABLE 1

| Entry | Compound used as a catalyst | loading | Time(s) to tan delta = 1 |
|---|---|---|---|
| 1 (comparative) | DBU | 7.5 ppm | 550 s |
| 2 (comparative) | DBU | 18 ppm | 250 s |
| 3 (comparative) | 1a | 21 ppm | 252 s |
| 4 (comparative) | urea | 2000 ppm | 1369 s |
| 5 (comparative) | 1b | 3333 ppm | 391 s |
| 6 (comparative) | 1,3-dimethyl-imidazolium chloride | 3333 ppm | 255 s |
| 7 (comparative) | 1-methylbenzimidazole | 420 ppm | >>2700 s |
| 8 (comparative) | 1-isopropylbenzimidazole | 420 ppm | >2700 s |
| 9 (comparative) | 4b | 420 ppm | no cure |
| 10 (comparative) | 4a | 420 ppm | no cure |
| 11 (comparative) | Zn(acac)$_2$ | 5000 ppm | >2700 s |
| 12 (comparative) | ZnO | 5000 ppm | >2700 s |
| 13 | 1 | 75 ppm | 256 s |
| 14 | 2 | 120 ppm | 268 s |
| 15 | 3 | 53 ppm | 268 s |
| 16 | 4 | 2400 ppm | 594 s |
| 17 | 5 | 3600 ppm | 1031 s |

Entry 1 and 2 in Table 1 showed standard base controls at different catalytic loadings. Entries 3-10 showed azolium salts or decomposed products. Entries 11 and 12 showed example zinc sources. Entries 13-17 showed the performance of Zn—NHC complexes as catalysts for the Ph-T-PhMe Resin Linear Copolymer.

In example 2, the same compounds were tested as catalysts with the same Ph-T-PhMe Resin Linear Copolymer as in example 1. However, a Yttrium Aluminum Garnet (YAG) phosphor was added to each sample. Each sample contained 1.5 g Resin Linear Copolymer and 1.5 g or more of the phosphor. The catalyst loading was based on the weight of the Ph-T-PhMe Resin Linear Copolymer. The cure profile was the same as in example 1. The results of the trials in the presence of the phosphor are shown below in Table 2.

TABLE 2

Zinc(NHC) catalyzed curing of Ph-T-PhMe Resin Linear Copolymers at 150° C. in the presence of phosphor fillers.

| Entry | Catalyst | loading | time to tan delta = 1 (with phosphor) | phosphor loading | time to tan delta = 1 (no phosphor) |
|---|---|---|---|---|---|
| 1 (comparative) | DBU | 7.5 ppm | no cure | 50 wt % | 550 s |
| 2 (comparative) | DBU | 18 ppm | >2700 s | 50 wt % | 250 s |
| 3 (comparative) | Zn(acac)$_2$ | 5000 ppm | >2700 s | 50 wt % | >2700 s |
| 4 (comparative) | ZnO | 5000 ppm | >2700 s | 50 wt % | >2700 s |
| 5 (comparative) | 1a | 21 ppm | >>2700 s | 50 wt % | 252 s |
| 6 | 1 | 75 ppm | 1417 s | 50 wt % | 256 s |
| 7 | 2 | 120 ppm | 373 s | 50 wt % | 268 s |
| 8 | 2 | 120 ppm | >>2700 s | 70 wt % | 268 s |
| 9 | 3 | 53 ppm | >2700 s | 50 wt % | 268 s |
| 10 | 4 | 2400 ppm | 1381 s | 70 wt % | 594 s |
| 11 (comparative) | Al(acac)$_3$ | 2400 ppm | 1165 s | 70 wt % | 965 s |

In example 2, entries 2, 5, 6, 7, 8, and 9 used catalyst loadings such that time to tan delta=1 were standardized with respect to one another (i.e., each used a loading such that in the sample with no phosphor, time to tan delta=1 was roughly constant at 250 to 270 seconds), which accounted for the difference in catalyst loadings, in order to draw conclusions about the inhibition effects of the phosphor. Note the difference between entries 6 and 5 with catalysts 1 and 1a in Table 2 which demonstrated the M-NHC complex provided superior catalytic effect to the NHC ligand alone. In addition the difference between the DBU control shown in entry 2 and the M-NHC complexes shown in entries 6 and 7 also demonstrated that the M-NHC complexes had better catalytic activity than the DBU control. Longer times to reach tan delta=1 without any phosphor present yielded much longer times to reach tan delta=1 with a phosphor loading of 50% or more. Entry 11 in Table 2, in which comparative catalyst Al(acac)$_3$, was used, exhibited little phosphor inhibition, however, other issues during curing, including phenyl-silicon cleavage to generate benzene would not allow Al(acac)$_3$ to be used as a catalyst for Ph-T-PhMe Resin Linear Copolymer in high temperature applications.

Table 3 summarizes the amount of benzene generated at 200° C. for the samples prepared as described above in Example 2. The samples were heated for 30 minutes at 200° C. in air. The amount of benzene was analyzed by GC of the headspace of the container for each sample. Large amounts of benzene correlated to undesirable film yellowing in practical applications. Relative to the comparative catalysts (which contained metals) tested, the M-NHC complexes 1-4 exhibited 10 times to 1000 times less benzene generation than the Al(acac)$_3$, Zn(acac)$_2$ and ZnO catalysts tested in this example. DBU and Al(acac)$_3$ represented the extremes of balancing benzene generation with phosphor inhibition, while the Zn(NHC) complexes represented a significant step forward in optimizing both properties.

TABLE 3

Amount of benzene generated at 200° C. with different catalysts in cured phenyl-T-PhMe resin-linear copolymers.

| Entry | Catalyst | ppm benzene |
|---|---|---|
| 1 (comparative) | No catalyst | <1 |
| 2 (comparative) | 50 ppm DBU | <1 |
| 3 (comparative) | 2400 ppm Al(acac)$_3$ | 5900 |
| 4 (comparative) | 5000 ppm Zn(acac)$_2$ | 640 |
| 5 (comparative) | 5000 ppm ZnO | 16 |
| 6 | 75 ppm 1 | 3 |
| 7 | 120 ppm 2 | 2 |
| 8 | 53 ppm 3 | 5 |
| 9 | 2400 ppm 4 | 49 |

In example 3, compositions were made using 0.1 M solutions of catalysts 2 and 3 shown above. Each 0.1 M solution of catalyst was made by dissolving the catalyst in toluene. Next, 0.24 g of the 0.1 M catalyst solution was added to 0.085 g polymethylhydridosiloxane (Mw=1900-2100) and 3.0 g of hydroxy-terminated polydimethylsiloxane (PDMS) (Mw=4200). The reactions were monitored at room temperature and 120° C., and the time to reach gellation was recorded. The results are shown below in Table 4.

TABLE 4

| Catalyst | Temperature | Time |
|---|---|---|
| 2 | RT | >2 h, partial cure, viscosity increase |
| 2 | 120 | 16 min |
| 3 | 120 | 11 min |

In example 4, compositions were made using 0.025 M solutions of catalyst 2 and catalyst 3 (and for comparative purposes, salt 1a). In each sample, 200 μL of a 0.025 M catalyst solution was added to 2.1 g silanol terminated PDMS and 0.136 g of Methyltrimethoxysilane. The reaction vessel was then covered with a thin film with a hole punctured in it and placed in a humidity chamber set at 50% relative humidity and 22° C. for 48 hours. The results are shown in Table 5.

TABLE 5

Zinc(NHC) catalyzed curing of MTM and PDMS

| entry | catalyst | cure |
|---|---|---|
| 1 | 2 | fully cured |
| 2 | 3 | increased viscosity |
| 3 (comparative) | 1a | increased viscosity |
| 4 (comparative) | 1a exposed to air | skinned over |

The invention claimed is:

1. A composition formed by mixing:
(A) a catalytically effective amount of a reaction product prepared by a method comprising combining
   i) a metal compound, where the metal compound is selected from a titanium compound and a zinc compound, and
   ii) an N-heterocyclic carbene; and
(B) a silanol functional compound having an average, per molecule, of one or more silicon bonded hydroxy moieties; and
where ingredient (A) catalyzes condensation reaction of the hydroxy moieties of ingredient (B).

2. The composition of claim 1, where the metal compound is a zinc(II) compound.

3. The composition of claim 1, where the metal compound is selected from dialkyl zinc compounds, diaryl zinc compounds, zinc dihalides, zinc dialkoxides, zinc diesters, and zinc(II) bis(trialkylsilyl)amides.

4. The composition of claim 2, where the zinc(II) compound is selected from bis-(pentamethylcyclopentadienyl) zinc, diethyl zinc, zinc dibutoxide, zinc diacetylacetonate, and $ZnCl_2$.

5. The composition of claim 1, where the N-heterocyclic carbene has general formula (I):

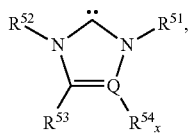

where Q is a nitrogen atom (N) or a carbon atom (C); subscript x is 0 when Q is N, and subscript x is 1 when Q is C; one of $R^{51}$ and $R^{52}$ is an alkyl group and the other of $R^{51}$ and $R^{52}$ is selected from the group consisting of an alkyl group, an hydroxy functional group, a carboxylic acid functional group, and a substituted or unsubstituted hydroxy functional aromatic group; and $R^{53}$ and $R^{54}$ are each independently selected from a hydrogen atom, an alkyl group, an alkenyl group, an alkynyl group, an aryl group or an aralkyl group, with the proviso that $R^{53}$ and $R^{54}$ may optionally bond together to form a fused ring structure.

6. The composition of claim 1, where the N-heterocyclic carbene is an imidazole based N-heterocyclic carbene ligand of formula (II):

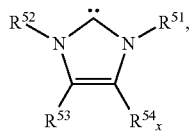

where subscript x is 1, one of $R^{51}$ and $R^{52}$ is an alkyl group and the other of $R^{51}$ and $R^{52}$ is selected from the group consisting of an alkyl group, an hydroxy functional group, a carboxylic acid functional group, and a substituted or unsubstituted hydroxy functional aromatic group; and $R^{53}$ and $R^{54}$ are each independently selected from a hydrogen atom, an alkyl group, an alkenyl group, an alkynyl group, an aryl group or an aralkyl group.

7. The composition of claim 1, where the N-heterocyclic carbene is an imidazole based N-heterocyclic carbene ligand of formula (III):

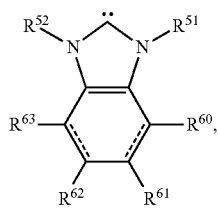

where one of $R^{51}$ and $R^{52}$ is an alkyl and the other of $R^{51}$ and $R^{52}$ is selected from the group consisting of an alkyl group, an hydroxy functional group, a carboxylic acid functional group, and a substituted or unsubstituted hydroxy functional aromatic group; and $R^{60}$, $R^{61}$, $R^{62}$, and $R^{63}$ are each independently selected from a hydrogen atom, an alkyl group, an alkenyl group, an alkynyl group, an aryl group or an aralkyl group.

8. The composition of claim 7, where each dashed line indicates a double bond, $R^{60}$, $R^{61}$, $R^{62}$, and $R^{63}$ are each independently selected from hydrogen or an alkyl group selected from methyl, ethyl, propyl or butyl.

9. The composition of claim 1, where the N-heterocyclic carbene is prepared by a method comprising combining an azolium salt with a base.

10. The composition of claim 9, where the azolium salt is selected from the group consisting of an azolium halide and an azolium borate.

11. The composition of claim 9, where the base is selected from the group consisting of cesium salts, KH, $K(N(SiMe_3)_3)_2$, NaOH, KOH, pyridine, lithiumdiisopropylamide, potassium t-butoxide, NaH, or $LiN(SiMe_3)_2$.

12. The composition of claim 1, where ingredient (A) comprises a complex of the general formula $[ML_n][X]_y$, where M is Zn or Ti, each L is selected from the group consisting of a halogen atom, a monovalent hydrocarbon group, an amino group, a silyl amide group, a carboxylate ester group, a hydrocarbonoxy group, and a N-heterocyclic carbene ligand, with the proviso that at least one L is the N-heterocyclic carbene ligand, and subscript n is 1 to the maximum number of attachment points to M regardless of the denticity or hapticity of the substituent for L, X is an unbound anion species to make the overall charge of the complex zero, and subscript y is 0 to 2 when M is Zn and subscript y is 0 to 4 when M is Ti.

13. The composition of claim 12, where ingredient (A) is a complex selected from the group consisting of:

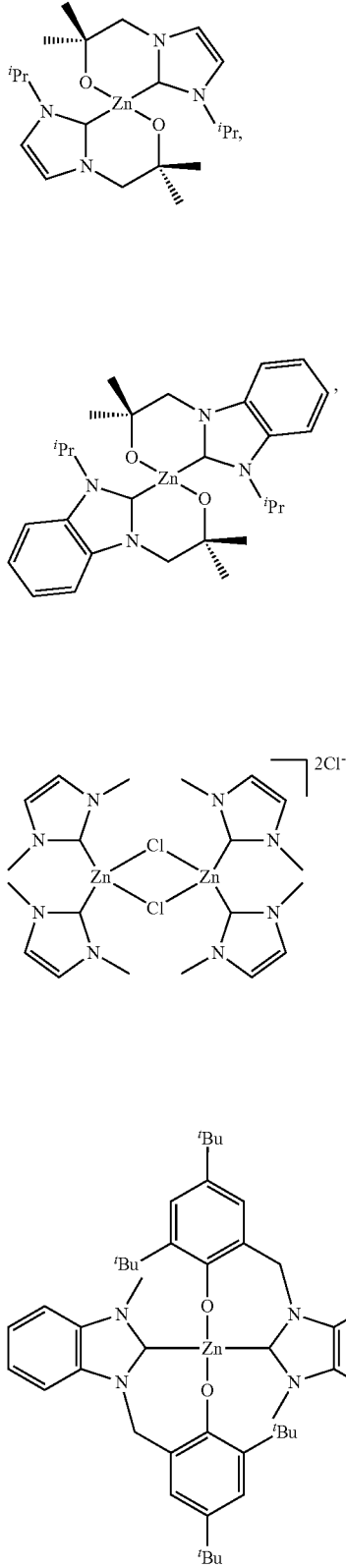

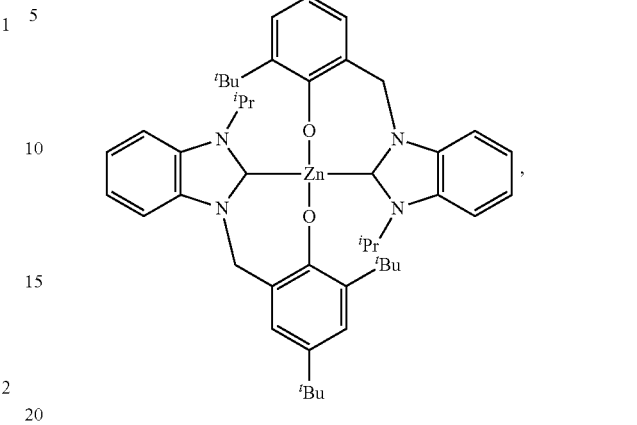

a cis isomer of any one of complexes 1, 2, 3, 4, and 5, and a mixture of two or more of cis and trans isomers of complexes 1, 2, 3, 4, and 5.

14. The composition of claim 1, where ingredient (B) comprises an organosiloxane block copolymer comprising:
40 to 90 mole percent disiloxy units of formula $[R^{71}_2SiO_{2/2}]$,
10 to 60 mole percent trisiloxy units of formula $[R^{72}SiO_{3/2}]$,
0.5 to 35 mole percent silanol groups $[\equiv SiOH]$;
where:
each $R^{71}$ and $R^{72}$ is independently a hydrocarbon group of 1 to 30 carbon atoms or a halogenated hydrocarbon group of 1 to 30 carbon atoms;
where:
the disiloxy units $[R^{71}_2SiO_{2/2}]$ are arranged in linear blocks having an average of from 10 to 400 disiloxy units $[R^{71}_2SiO_{2/2}]$ per linear block,
the trisiloxy units $[Fl^{72}SiO_{3/2}]$ are arranged in non-linear blocks having a molecular weight of at least 500 g/mole, and at least 30% of the non-linear blocks are crosslinked with each other, each linear block is linked to at least one non-linear block; and
the organosiloxane block copolymer has a weight average molecular weight of at least 20,000 g/mole.

15. The composition of claim 1, further comprising a filler.

16. The composition of claim 15, where the filler comprises a phosphor.

17. The composition of claim 1, further comprising a crosslinker.

18. The composition of claim 17, where the crosslinker is an alkoxysilane or a polyorganohydrogensiloxane.

19. A method comprising: exposing to moisture, a composition formed by mixing:
(A) a catalytically effective amount of a reaction product prepared by a method comprising combining
i) a metal compound, where the metal compound is selected from a titanium compound and a zinc compound, and
ii) an N-heterocyclic carbene; and
(B) a silanol functional compound having an average, per molecule, of one or more silicon bonded hydroxy moieties; and
where ingredient (A) catalyzes condensation reaction of the hydroxy moieties of ingredient (B); thereby preparing a reaction product.

* * * * *